(12) United States Patent
Rocha-Singh et al.

(10) Patent No.: US 10,123,786 B2
(45) Date of Patent: Nov. 13, 2018

(54) BONE MARROW HARVESTING DEVICE

(71) Applicant: Krishna Rocha-Singh, Springfield, IL (US)

(72) Inventors: Krishna Rocha-Singh, Springfield, IL (US); Michael Hogendijk, Santa Rosa, CA (US)

(73) Assignee: Krishna Rocha-Singh, M.D., Springfield, IL (US)

( * ) Notice: Subject to any disclaimer, the term of this patent is extended or adjusted under 35 U.S.C. 154(b) by 0 days.

(21) Appl. No.: 15/429,059

(22) Filed: Feb. 9, 2017

(65) Prior Publication Data
US 2018/0078243 A1  Mar. 22, 2018

Related U.S. Application Data

(60) Provisional application No. 62/395,772, filed on Sep. 16, 2016.

(51) Int. Cl.
*A61B 10/02* (2006.01)
*A61B 17/22* (2006.01)
(Continued)

(52) U.S. Cl.
CPC ........ *A61B 10/025* (2013.01); *A61B 17/1635* (2013.01); *A61B 17/221* (2013.01);
(Continued)

(58) Field of Classification Search
CPC .. A61F 2/4611; A61F 2/4601; A61B 17/8855; A61B 18/1492; A61M 25/10
See application file for complete search history.

(56) References Cited

U.S. PATENT DOCUMENTS 2,701,559 A  *  2/1955  Cooper ................. A61B 10/02
                                                        15/104.33
5,300,070 A       4/1994  Gentelia et al.
                        (Continued)

FOREIGN PATENT DOCUMENTS

WO   WO-2008/103839 A2   8/2008
WO   WO-2012/088167 A2   6/2012

OTHER PUBLICATIONS

International Search Report & Written Opinion dated Dec. 15, 2017 in Int'l PCT Patent Appl. No. PCT/US17/051576.

*Primary Examiner* — Sean Dougherty
*Assistant Examiner* — Patrick Fernandes
(74) *Attorney, Agent, or Firm* — Foley & Lardner LLP; Christopher C. Bolten; Nicola A. Pisano

(57) ABSTRACT

Bone marrow harvesting devices and methods of use for harvesting bone marrow from a biological source of bone marrow are provided that promote ease of use, and reduce patient pain and potential trauma to harvested bone marrow, wherein an exemplary bone marrow harvesting device includes an elongated shaft comprising a distal region, a proximal region, and a lumen extending therebetween, the distal region comprising a plurality of through-wall apertures in fluid communication with the lumen; and an expandable member disposed along the distal region thereof and configured to transition between a collapsed state and an expanded state for vibrating to disrupt the bone marrow. Methods of using the inventive bone marrow harvesting device to provide more efficient bone marrow disruption, improve the efficiency of bone marrow aspiration, and increase the quantity of bone marrow harvested in a single procedure are also provided.

20 Claims, 17 Drawing Sheets

(51) Int. Cl.
  A61M 1/00 (2006.01)
  A61B 17/221 (2006.01)
  A61M 25/00 (2006.01)
  A61B 17/16 (2006.01)
  *A61B 90/00* (2016.01)
  *A61B 17/00* (2006.01)
  *A61B 17/32* (2006.01)
  *A61B 10/00* (2006.01)

(52) U.S. Cl.
  CPC ......... A61B 17/2202 (2013.01); A61M 1/008 (2013.01); A61M 25/0074 (2013.01); *A61B 10/0096* (2013.01); *A61B 10/0283* (2013.01); *A61B 2010/0258* (2013.01); *A61B 2017/00867* (2013.01); *A61B 2017/00969* (2013.01); *A61B 2017/22079* (2013.01); *A61B 2017/320024* (2013.01); *A61B 2017/320076* (2013.01); *A61B 2090/376* (2016.02); *A61B 2090/3916* (2016.02); *A61B 2090/3966* (2016.02); *A61B 2217/005* (2013.01); *A61M 2025/0096* (2013.01); *A61M 2202/10* (2013.01)

(56) References Cited

U.S. PATENT DOCUMENTS

| | | |
|---|---|---|
| 5,385,151 A | 1/1995 | Scarfone et al. |
| 5,472,017 A | 12/1995 | Kovalcheck |
| 5,782,764 A | 7/1998 | Werne |
| 5,820,594 A * | 10/1998 | Fontirroche ...... A61M 25/0009 604/165.01 |
| 5,865,800 A | 2/1999 | Mirarchi et al. |
| 6,066,153 A | 5/2000 | Lev |
| 6,337,994 B1 | 1/2002 | Stoianovici et al. |
| 6,902,540 B2 | 6/2005 | Dorros et al. |
| 7,092,488 B2 | 8/2006 | Richardson |
| 7,122,020 B2 | 10/2006 | Mogul |
| 7,399,306 B2 | 7/2008 | Reiley et al. |
| 7,462,181 B2 | 12/2008 | Kraft et al. |
| 7,998,112 B2 | 8/2011 | Chow et al. |
| 8,795,306 B2 | 8/2014 | Smith et al. |
| 9,089,347 B2 | 7/2015 | Sankaran et al. |
| 2005/0209530 A1 | 9/2005 | Pflueger |
| 2007/0055282 A1 | 3/2007 | Muschler |
| 2007/0191766 A1* | 8/2007 | McMorrow ........... A61M 25/10 604/103.01 |
| 2007/0198043 A1 | 8/2007 | Cox et al. |
| 2007/0276352 A1 | 11/2007 | Crocker et al. |
| 2008/0009747 A1* | 1/2008 | Saadat ................. A61B 1/0008 600/471 |
| 2008/0214957 A1 | 9/2008 | Verra et al. |
| 2008/0243111 A1* | 10/2008 | Gammie ................ A61B 18/02 606/21 |
| 2008/0294044 A1* | 11/2008 | Voic ............... A61B 17/320068 600/439 |
| 2010/0069786 A1 | 3/2010 | Globerman et al. |
| 2012/0289982 A1* | 11/2012 | Gunday ......... A61B 17/320725 606/159 |
| 2013/0096587 A1 | 4/2013 | Smith et al. |
| 2014/0296742 A1* | 10/2014 | Kalloo ............. A61B 17/32002 600/570 |
| 2014/0316402 A1* | 10/2014 | Shah ................. A61B 18/1492 606/34 |

* cited by examiner

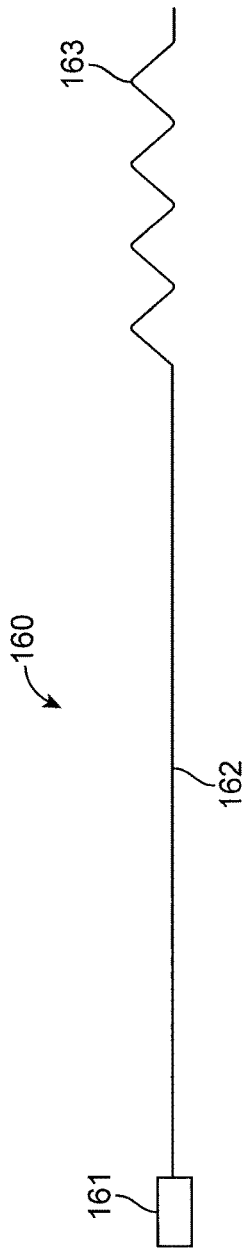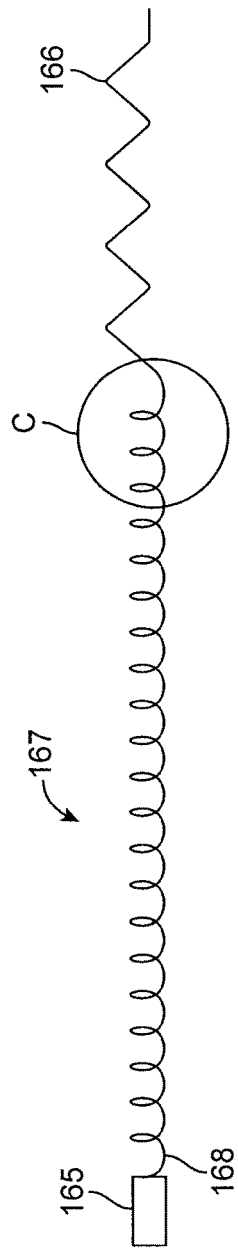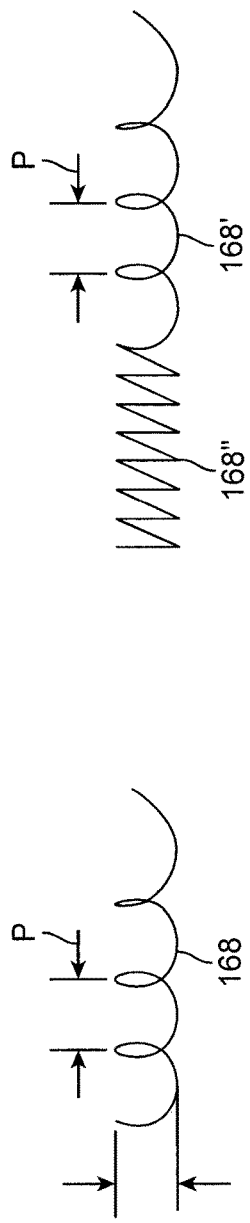

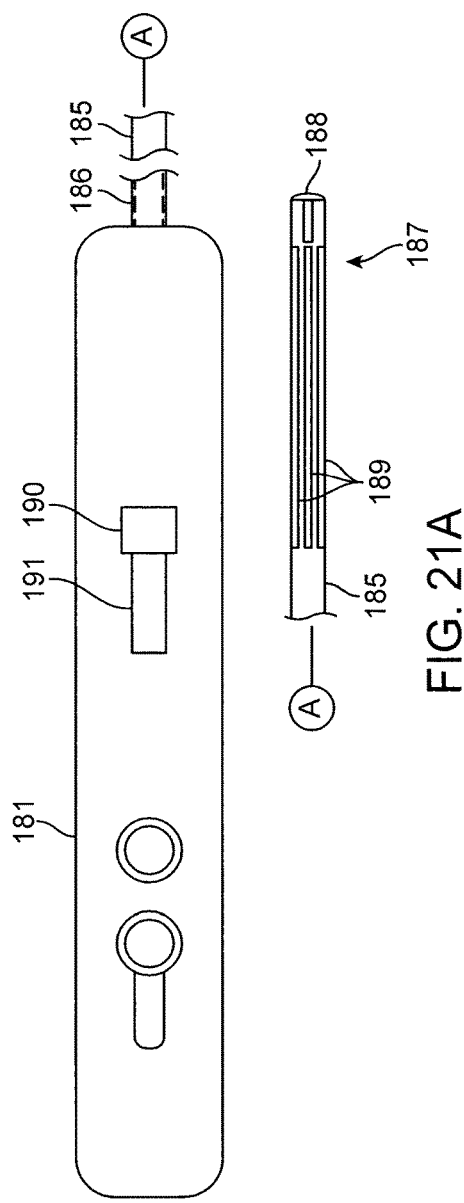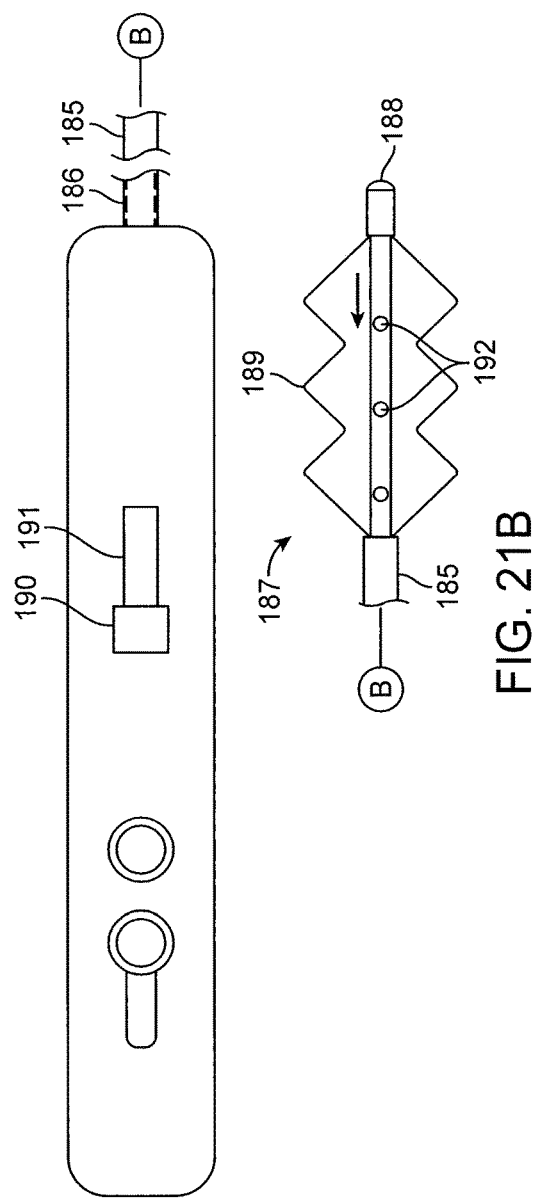

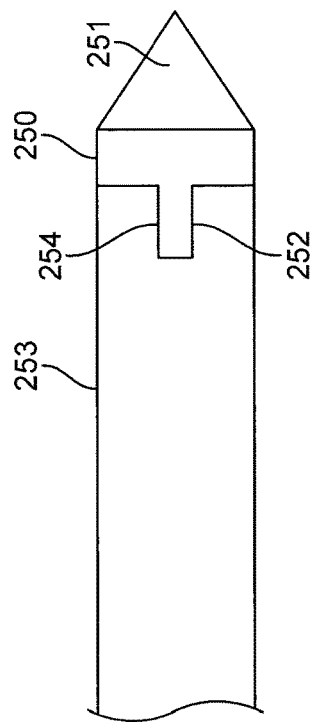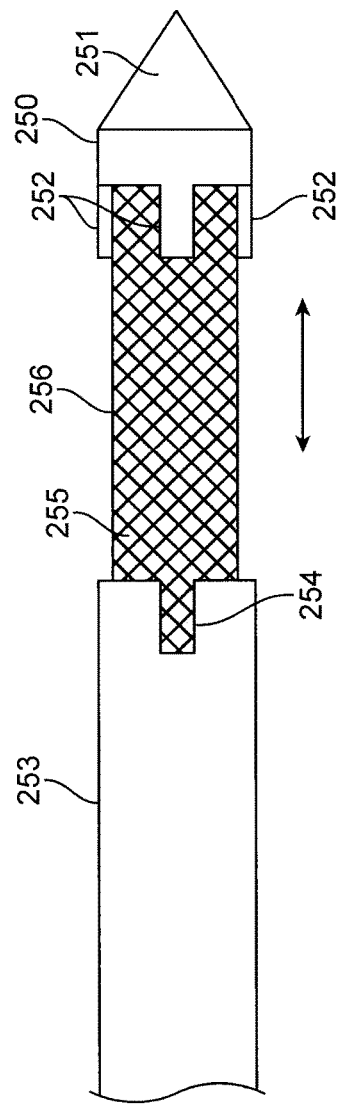
FIG. 26A
FIG. 26B

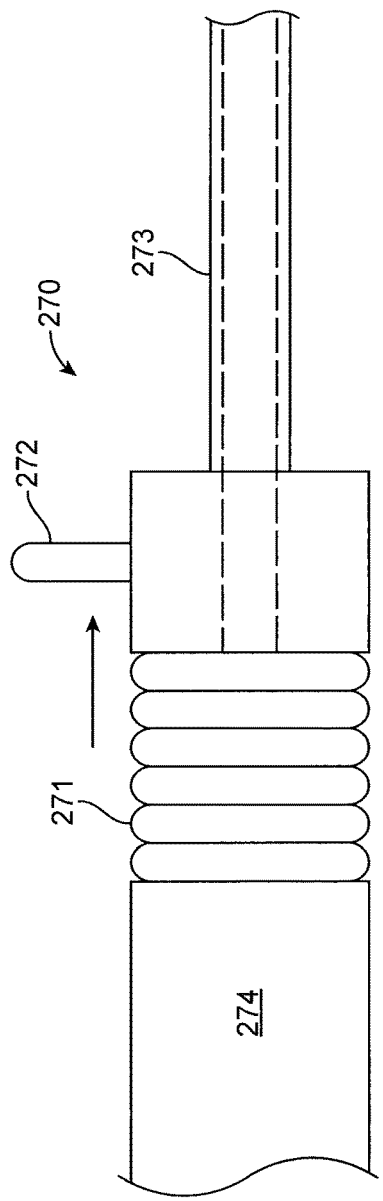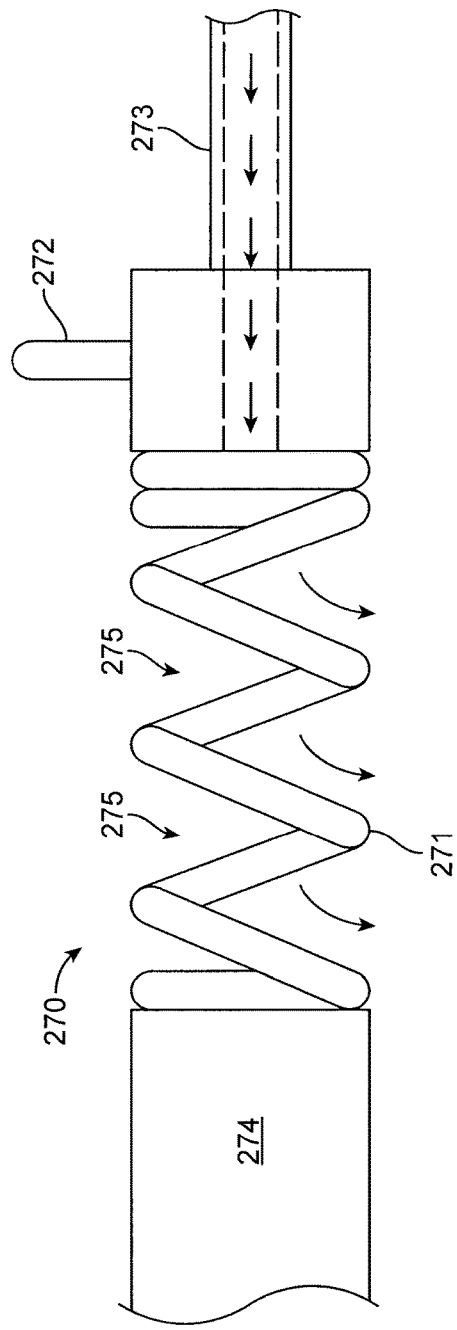
FIG. 28A
FIG. 28B

BONE MARROW HARVESTING DEVICE

CROSS REFERENCE TO RELATED APPLICATIONS

This application claims the benefit under 35 U.S.C. § 119(e) of U.S. Provisional Application Ser. No. 62/395,772, filed Sep. 16, 2016, the content of which is hereby incorporated by reference in its entirety.

TECHNICAL FIELD

The present invention is directed to apparatus and methods for extracting bone marrow from a patient body while minimizing rupture of the cells contained within that bone marrow.

BACKGROUND OF THE INVENTION

Bone marrow is the spongy tissue found in the interior of some types of bones, such as the pelvis, sternum, cranium, ribs, vertebrae and scapulae. Bone marrow is a rich reservoir for pluripotent hematopoietic stem cells, which can be used for stem cell therapy. Conventional bone marrow harvesting devices, such as Jamshidi™ bone marrow needle, generally include a cannula, a handle at the proximal end of the cannula used by a physician to apply force to the cannula, and a stylet with a sharp distal tip to penetrate the bone. During an operation, a physician accesses the target bone, typically from the iliac crest, and applies a suction force to aspirate bone marrow into the cannula.

Bone marrow density varies from patient to patient, where high bone marrow density is typical associated with young age, and calcification of the cancellous bone tissue. Conventional bone marrow harvesting devices may produce insufficient suction force to extract bone marrow in high bone marrow density areas and may be inefficient when a large quantity of bone marrow is required for stem cell therapy or autologous bone marrow transplantation. Several alternative designs have been proposed to facilitate aspiration of bone marrow. For example, U.S. Pat. No. 6,066,153 to Lev and U.S. Patent Publication No. 2005/0209530 to Pflueger each discloses a cutting tip having an "Archimedes' screw" configuration disposed inside the distal end of a cannula. The cutting tip, when rotated, dissects tissue and pushes the dissected tissue proximally, which can be aspirated. In another example, U.S. Patent Publication No. 2007/0198043 to Cox discloses a rotatable aspiration needle and a resilient wire with a curved distal portion disposed in the lumen of the cannula, for agitating or breaking-up bone marrow tissue to facilitate aspiration. However, rotational force may traumatize and/or rupture the stem cells located within the bone marrow, thus requiring a balance to be stuck between causing sufficient disruption of the bone marrow to permit aspiration while reducing trauma to the constituents of the bone marrow.

In view of the foregoing drawbacks of previously known bone marrow aspiration apparatus and methods, there exists a need for a safe and efficacious bone marrow harvesting device that facilitates aspiration of bone marrow, especially in dense tissue, while reducing trauma to the bone marrow constituents.

SUMMARY OF THE INVENTION

In view of the aforementioned drawbacks of previously known bone marrow aspiration methods and apparatus, the present invention provides apparatus and methods for harvesting bone marrow from a patient body. In accordance with one aspect of the disclosure, an expandable member coupled to a vibrational source is used to disrupt the bone marrow in a target site of a patient body by vibrating the expandable member. The use of vibration is expected to provide more efficient bone marrow disruption while causing less trauma, thereby improving the efficiency of bone marrow aspiration, and increasing the quantity of medically useful bone marrow that may be harvested in a single procedure. In accordance with one aspect of the present invention, the pattern of the expandable member may be selected and adjusted to optimize the area and/or intensity of vibration to facilitate bone marrow aspiration from the target site. In accordance with another aspect of the present invention, a motorized module and a vibrational module may be removably coupled to the device to provide drilling and vibrational force for performing bone marrow aspiration. Alternatively, the motorized module and the vibrational module may include the same motive components embedded in the device.

Apparatus and methods are provided for bone marrow aspiration that advantageously create a closed sterile system for extracting bone marrow and injecting a liquid into the target site to improve bone marrow disruption, facilitate bone marrow extraction, and which additionally may provide therapeutic treatment.

Apparatus and methods are further provided such that the position and orientation of the distal end of the bone marrow harvesting device may be ascertained using radiopaque markers and fiducial marks. In one aspect, the markers constitute an improvement over conventional bone marrow harvesting devices, which typically are conducted blindly and are largely dependent on the clinician's feel and experience, which may lead to severe pain or discomfort, excessive bleeding, or even infection.

In accordance with one aspect of the invention, a bone marrow harvesting device is provided comprising an elongated shaft having a distal region, a proximal region, and a lumen extending therebetween. The distal region of the shaft, which may be deflectable, includes a plurality of through-wall apertures in fluid communication with the lumen. An expandable member is disposed along the distal region and is configured to transition between a collapsed configuration for insertion into a biological source of bone marrow and/or for penetrating tissue, and an expanded configuration for disrupting the bone marrow. The expandable member is configured to vibrate to disrupt the bone marrow. At least one of the plurality of through-wall apertures may be located within the expandable member, when in the expanded configuration, to collect disrupted bone marrow.

The bone marrow harvesting device also may include an outer sheath slidably disposed on the elongated shaft, such that the expandable member may be expanded by moving the elongate shaft relative to the outer sheath, i.e., either retracting the outer sheath or advancing the elongated shaft from within the outer sheath. The handle includes an actuator to transition the expandable member between the collapsed configuration and the expanded configuration. The actuator may include a cylindrical element disposed proximal or distal to, and coupled to, the expandable member, such that the expandable member may be expanded by pushing, pulling, twisting the cylindrical element, or by a combination of such motions. The actuator further may comprise a knob coupled to the proximal end of the expandable member, such that pulling or pushing the knob may expand or collapse the expandable member.

The elongated shaft may include a drill bit attached to its distal end, such that a motor coupled to a proximal end of the elongated shaft via a suitable gear arrangement may rotate the drill bit to penetrate body tissue to reach a source of bone marrow.

The expandable member may include a plurality of wires, each having a zig-zag pattern. The plurality of wires may be made of a shape memory alloy. The expandable member also may comprise an expandable braided cage. A vibrational source further may be coupled to the expandable member, and includes at least one of an ultrasonic transducer, a piezoelectric transducer, a vibration motor, and a linear resonant actuator.

The bone marrow harvesting device also may include an aspiration lumen coupled to a reservoir, disposed in the proximal region of the elongated shaft and in fluid communication with the lumen and apertures disposed in the distal region of the elongated shaft. A valve may be disposed between the aspiration member and the lumen to control the application of suction through the lumen of the elongated shaft to collect disrupted bone marrow via the apertures in the distal region.

At least a portion of the distal region of the bone marrow harvesting device may include at least one radiopaque marker. The bone marrow harvesting device also may include at least one fiducial mark disposed on the proximal region of the elongated shaft.

Methods of harvesting bone marrow from a patient also are provided, in which the bone marrow harvesting device is advanced to a biological source of bone marrow in the patient. An expandable member disposed over the distal portion of the elongated shaft may be expanded and then vibrated to disrupt the bone marrow. Disrupted bone marrow then is extracted through at least one of the plurality of through-wall apertures disposed on the elongated shaft, and into the lumen of the elongated shaft. The bone marrow then is moved through the lumen to a reservoir for storage and future use.

The methods further may include introducing a liquid through the lumen of the elongated shaft to the biological source of bone marrow. The liquid may be at least one of saline, heparinized saline, lactated ringer solution, growth factors, anti-inflammatory agents, antibiotics, analgesic agents, nucleic acids, cells, and any combinations thereof.

BRIEF DESCRIPTION OF THE DRAWINGS

FIG. 16 is a side view of one embodiment of a vibration assembly in accordance with the principles of the present invention.

FIG. 17 is a side view of another embodiment of a vibration assembly in accordance with the principles of the present invention.

FIGS. 18A-18B are enlarged views of portion C depicted in FIG. 17.

FIGS. 21A and 21B are, respectively, top views of the bone marrow harvesting device of FIG. 20 with the expandable member in a collapsed state and expanded configuration.

FIGS. 26A-26B show an embodiment of the expandable member and drilling tip of a bone marrow harvesting device of the present invention in lock/unlocked configuration.

FIGS. 28A and 28B are, respectively, side views of a portion of an alternative embodiment of a bone marrow harvesting device in drilling and aspiration modes of operation.

DETAILED DESCRIPTION OF THE PREFERRED EMBODIMENTS

Figure 1:
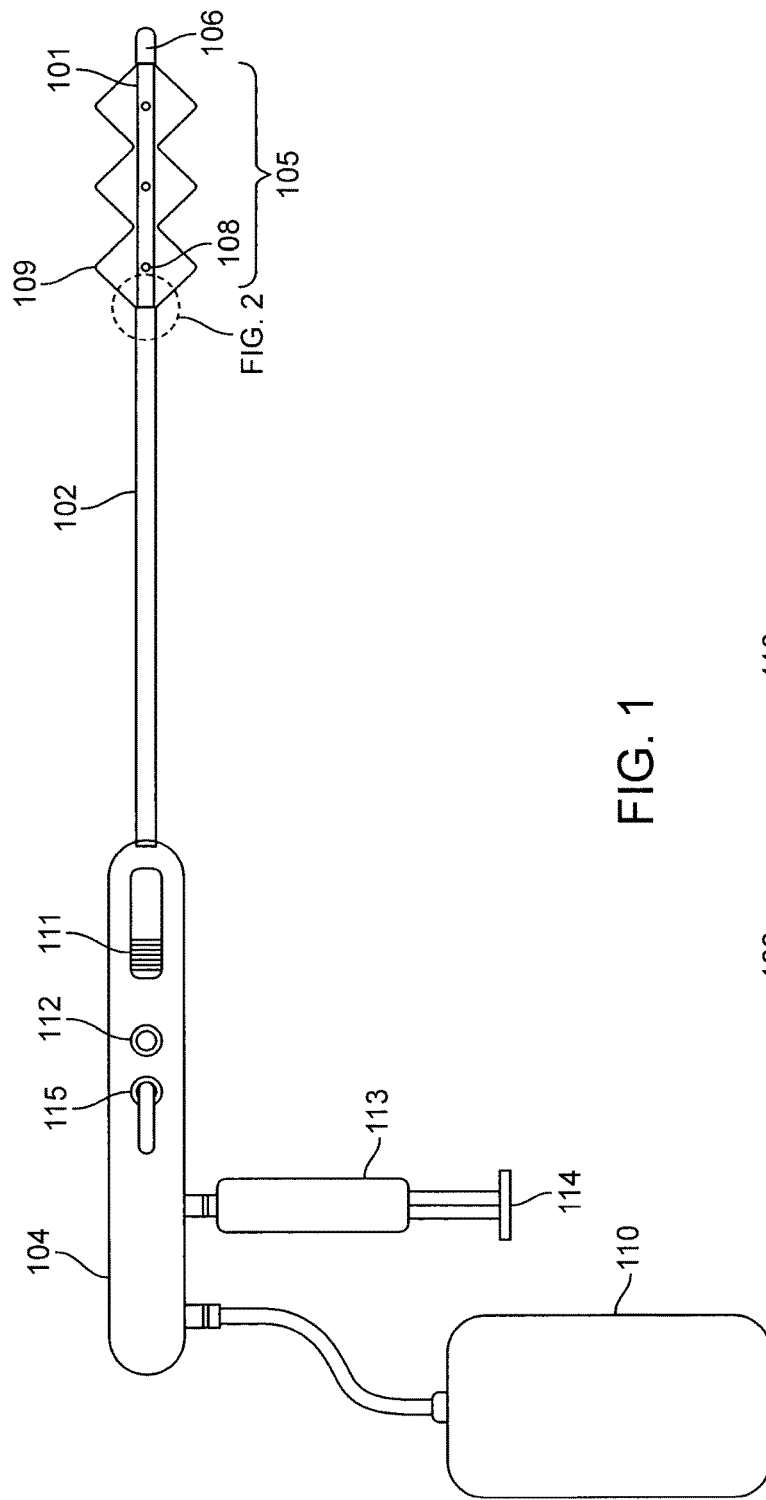
FIG. 1 is a schematic view of an illustrative bone marrow harvesting device constructed in accordance with the principles of the present invention.
Figure 2:
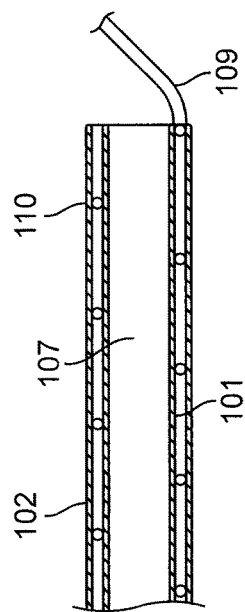
FIG. 2 is an enlarged view of the distal end of the outer sheath of FIG. 1.

Referring to FIGS. 1 and 2, a bone marrow harvesting device constructed in accordance with the principles of the present invention is described. Bone marrow harvesting device 100 has elongated shaft 101 slidably disposed within outer sheath 102. Elongated shaft 101 includes a proximal end attached to actuator 111 disposed in housing 104, distal region 105 having distal end 106, and lumen 107 extending between the proximal end and distal end 106. Distal region 105 has a plurality of through-wall apertures 108 disposed on elongated shaft 101 and in fluid communication with lumen 107, and expandable member 109 disposed along distal region 105. Housing 104 further may include a vibrational source (not shown), aspiration member 113 for applying suction force, reservoir 110 for containing extracted bone marrow, and actuator 111 for expanding and collapsing expandable member 109 and irrigation port 112. Aspiration member may be a conventional vacuum pump, or syringe 113 having plunger 114. Stopcock 115 controls fluid flow between apertures 108 of elongated shaft 101, syringe 113 and reservoir 110.

Still referring to FIG. 1, in a preferred embodiment, expandable member 109 comprises a plurality of wires disposed along distal region 105. In one embodiment, the plurality of wires may each have a zig-zag form. When expanded, the plurality of wires assume a "saw tooth" configuration when viewed from the side, with the apexes oriented perpendicular to the longitudinal axis of elongated shaft 101.

Bone marrow harvesting device 100 may be inserted through a trocar cannula. As is conventional in use of trocars, an obturator first may be inserted into the cannula to penetrate patient body to the target area where bone marrow aspiration is desired. The obturator then is retracted and replaced with bone marrow harvesting device 100.

Distal tip 106 may be closed and may include a sharpened tip for penetration or navigating the tissue. Alternatively, distal tip 106 may be open and in fluid communication with lumen 107, so that bone marrow also may be directly aspirated through the opening in the distal tip. Lumen 107 of elongated shaft 101, together with the opening in distal tip 106, may allow for the insertion of other tools to loosen or manipulate the bone marrow using a Y-arm assembly on housing 104 (not shown).

Distal tip 106 and the distal region 105 may be deflectable, for example, using pull wires or other mechanisms known in the art. Having a deflectable distal section allows the shape of distal region 105 to be temporarily altered to allow for bone marrow aspiration from different locations and/or directions from a target site. For example, elongated shaft 101 may be made of a flexible material, or may be heat set into a curved configuration. Alternatively, distal region 105 may be made of a memory metal such as nitinol tubing, and could be heat set to have a slightly curved shape.

The plurality of through-wall apertures 108 may be disposed in a linear, radial, helical or other pattern in distal region 105, and apertures 108 may be of any suitable shape, for example, round, elliptical, octagonal, etc., although having a smooth circumference is generally expected to be preferred. The plurality of through-wall apertures 108 may be of any number, of different sizes, or have gradually increasing diameter in a proximal to distal direction along distal region 105. In accordance with one aspect of the present invention, the through-wall apertures 108 preferably are radiused to avoid sharp edges that might cause mechanical damage to the bone marrow during aspiration. In one preferred embodiment, the through-wall apertures 108 are aligned in a helical array to resist kinking or buckling of elongated shaft 101 during use. While FIG. 1 shows three apertures disposed in distal region 105, it should be understood that any number of apertures may be used. As will be apparent to one of ordinary skill based on the description provided in this disclosure, the diameters of the apertures may be determined by the size of the catheter and/or the volume of the bone marrow to be harvested.

The plurality of wires of expandable member 109 preferably intersect at the proximal end of distal region 105 or distal end of outer sheath 102 such that when distal region 105 of elongated shaft 101 is advanced distally beyond the end of outer sheath 102, expandable member 109 assumes an expanded configuration. Expandable member 109 also may self-expand when outer sheath 102 is retracted proximally to uncover distal region 105. Alternatively, expandable member 109 may be reversibly expanded by pulling, pushing, or any other mechanism known in the art. Expandable member 109 may be expanded when distal region 105 is placed in a target site in a patient body, which provides a biological source of bone marrow. Alternatively, expandable member 109 may be expanded during penetration, before reaching a target site, to disrupt dense tissue.

Housing 104 also may include irrigation port 112 and stopcock 115, both in fluid communication with lumen 107 of elongated shaft 101. Irrigation port 112 permits a syringe filled with an irrigation fluid, such as saline, to be injected via lumen 107 and apertures 108 to facilitate aspiration of bone marrow. Stopcock 115, as described below, selectively connects syringe 113 to either lumen 107 or reservoir 110. When conducting bone marrow aspiration, stopcock 115 is opened to permit retraction of plunger 114 to aspirate bone marrow through apertures 108 and lumen 107 into syringe 113. Stopcock 115 then is closed to disconnect syringe 113 from lumen 107, so that when plunger 114 is pushed into the body of syringe 113, bone marrow contained within the syringe is pushed into reservoir 110. As described in detail below, housing 104 include one-way valves disposed in fluid communication with lumen 107 and the flow path to reservoir that prevent backflow from syringe 113 to lumen 107.

Actuator 111 selectively expands or collapses expandable member 109. In the embodiment of FIG. 1, actuator 111 is in the form of a knob coupled to the proximal end of elongated shaft 101, which is configured to reciprocate longitudinally to expand or collapse expandable member 109. Alternatively, actuator 111 may comprise a wire, a suture or any other mechanism known in the art, such that expansion and contraction of expandable member 109 may be accomplished by pulling, pushing or twisting actuator 111.

Housing 104 preferably is coupled to an aspiration member, e.g., vacuum pump or other device that provides a suction force, to aspirate bone marrow through apertures 108 in distal region 105. In the embodiment of FIG. 1, aspiration is accomplished by retracting plunger 114 of syringe 113.

In another aspect of the invention, the aspiration member also may be configured to inject a liquid through lumen 107 and into the target site being aspirated. Preferably, syringe 113 and plunger 114 creates a closed sterile system for infusion of liquid and aspiration of bone marrow. Advantageously, liquid may be injected via irrigation port 112, lumen 107 and apertures 108 into the target site to make up for marrow volume loss, and to facilitate bone marrow aspiration. Injection of liquid also may increase resonance and vibration intensity, which may be desirable for disrupting and facilitating aspiration of denser bone marrow. Additionally, the injected liquid may include a saline solution, a therapeutic agent providing analgesic effect, a biologic that promotes bone marrow regrowth, or any combination thereof. The saline solution may be saline, heparinized saline or lactated ringer solution. The therapeutic agent may include anti-inflammatory agents, antibiotics, and analgesic agents. The biologic, if present, may consist of growth factors, nucleic acids, and/or cells such as autologous red blood cells.

Syringe 113 preferably is a Luer lock syringe to facilitate ease of assembly and single-use disposal of this component. In a locked position, syringe 113 enables application of a relatively constant suction, which is proportional to the size of the syringe. Syringe 113 may be of any size that provides a desired amount of aspiration of bone marrow or injection of a liquid to the target site, for example, 10 cc or 20 cc.

Elongated shaft 101 and outer sheath 102 preferably are constructed such that their respective distal ends or regions are visibly different from one another when observed under clinical imaging modalities. For example, elongated shaft 101 and outer sheath 102 may have different degrees of radio-opacity, or have some other observable difference that makes them distinguishable when both are viewed under fluoroscopy visualization. Housing 104 also may include one or more fiducial marks that indicate the position, orientation of distal region 105 or the degree of expansion of expandable member 109.

Outer sheath 102 and elongated shaft 101 each preferably have a length and diameter suitable for use with intended target sites, such as the posterior iliac crest, and for collecting a desired amount of bone marrow. For example, outer sheath 102 and elongated shaft 101 may be about 5 cm to about 15 cm in length, with a diameter from about 8 gauge to about 15 gauge. Distal region 105 preferably has a length of about 0.1 cm to about 3.0 cm. Outer sheath 102 and elongated shaft 101 may be formed of conventional materials of construction, e.g., a plastic material such as polyethylene, polyvinylchloride, polyesters or the like. Expandable member 109 may be permanently coupled to elongated shaft 101 or may be manufactured as a separate piece and coupled to the device prior to use.

The vibrational source may comprise at least one of an ultrasonic transducer, a piezoelectric transducer, a vibratory motor, and a linear resonant actuator. The vibrational source may be disposed within housing 104, or more preferably removably coupled to housing 104 or expandable member 109. Vibration of the expandable member may be activated before and/or during aspiration.

After a desired amount of bone marrow has been harvested, or after vibration is completed, expandable member 109 may be collapsed in a manner consistent with the expansion mechanisms described above. Expandable member 109 preferably may be collapsed by advancing elongated shaft 101 distally. Expandable member 109 also may be collapsed by re-advancing outer sheath 102. Alternatively, expandable member 109 may be collapsed by pulling, pushing or twisting the expandable member.

Still referring to FIG. 2, a sectional view of elongated shaft 101, outer sheath 102 and expandable member 109 constructed in accordance with the principles of the present invention is described, showing one of the plurality of wires of expandable member 109 helically disposed in an annulus defined by an inner surface of outer sheath 102, and an outer surface of elongated shaft 101. The plurality of wires is securely attached to elongated shaft 101 such that when distal region 105 of elongated shaft 101 is advanced distally, the plurality of wires extends beyond the distal end of outer sheath 102 and assumes a deployed state.

Figure 3:
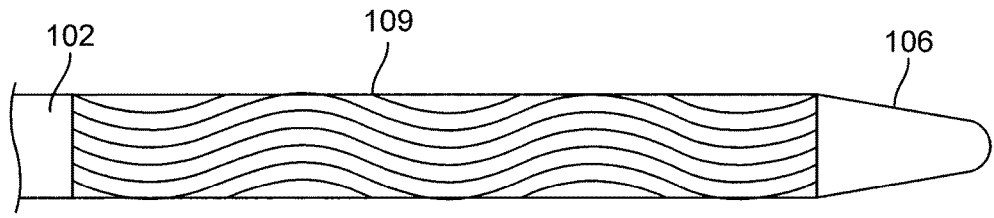
FIG. 3 is a side view of the expandable member of FIG. 1 in a collapsed state.
Figure 4:
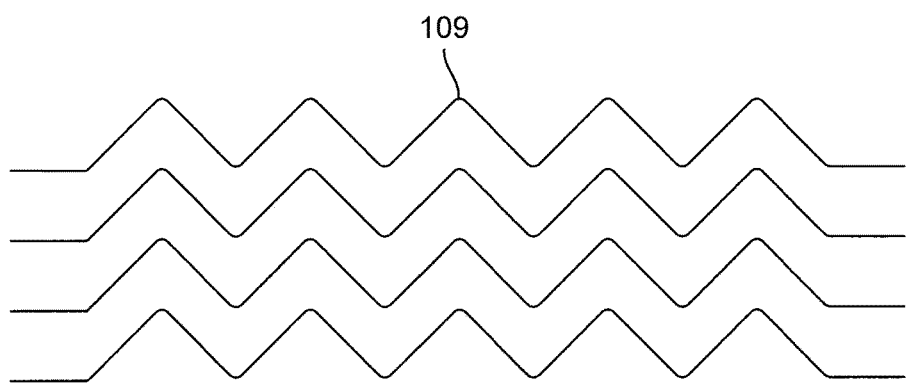
FIG. 4 is a plan view of the expandable member of the bone marrow harvesting device in FIG. 1 in an expanded flattened configuration in accordance with the principles of the present invention.
Figure 5:
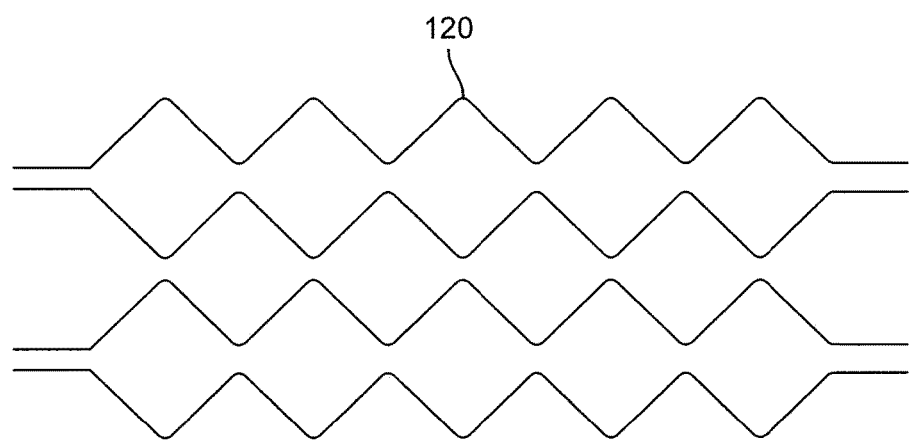
FIG. 5 is a plan view of an alternative embodiment of the expandable member of the present invention in an expanded flattened configuration.

In FIG. 3, the plurality of wires is elongated along distal region 105 of elongated shaft 101 to assume a collapsed state. FIG. 4 depicts a first patterns of the plurality of wires of expandable member 109 in the deployed position, in which the zig-zag pattern of adjacent wires is aligned, thereby creating a uniform gap between adjacent wires. FIG. 5 depicts an alternative embodiment of an expandable member, expandable member 120, in which the zig-zags of adjacent wires are out of phase, i.e., oppositely aligned, so such that adjacent wires create diamond shapes when deployed.

Figure 6:
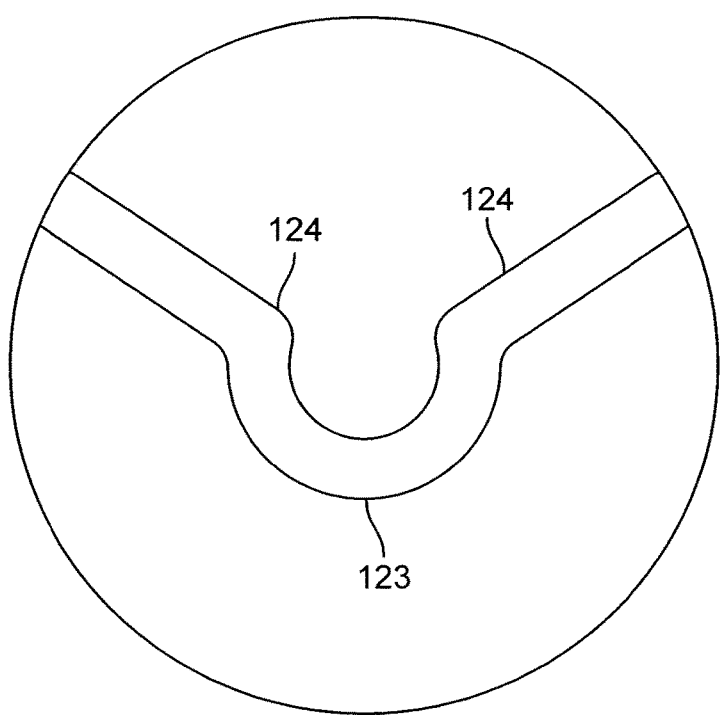
FIGS. 6-10 are illustrative patterns for alternative embodiments of the plurality of wires employed in an expandable member constructed in accordance with the principles of the present invention.
Figure 7:
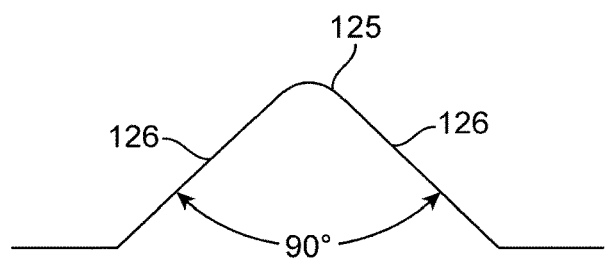
Figure 8:
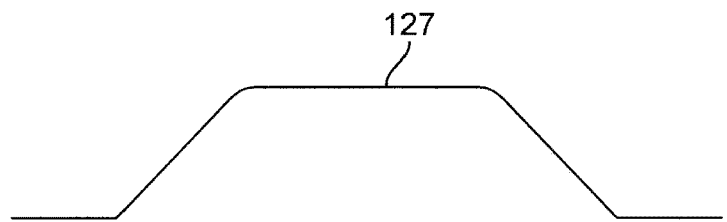
Figure 9:
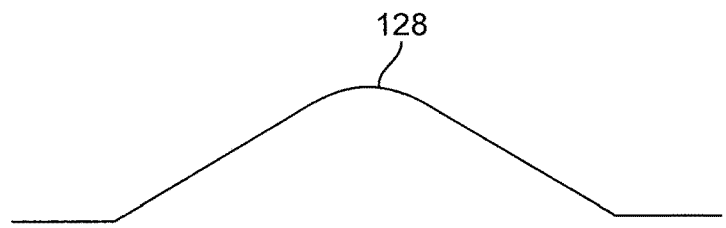
Figure 10:
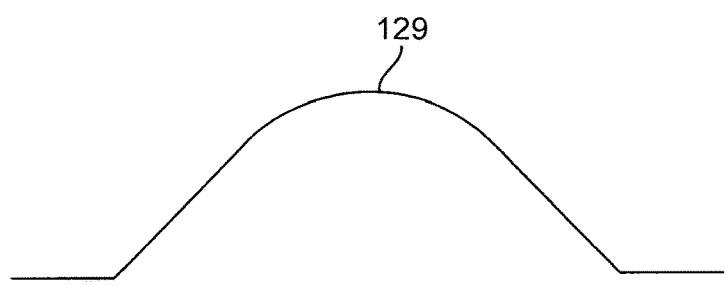

Referring now to FIGS. 6 to 10, other patterns of the plurality of wires in alternative embodiments of expandable member 109 of the present invention are described. In FIG. 6, each wire 122 of an expandable member includes zig-zags having bend 123 connected by two struts 124. As depicted in FIG. 7, the angle of bend 125 between two adjacent struts 126 may be from about 90 degrees to about 180 degrees. The bend also may be an arc having an arc length that is longer or shorter than that of the adjacent struts. The bend further may be in the form of trapezoid 127, as depicted in FIG. 8, peak 128 as depicted in FIG. 9, sinusoid 129 as depicted in FIG. 10, or any other shape. In accordance with one aspect of the present invention, the pattern of the zig-zag wires and the patterns of the plurality of wires determine the area and intensity of the vibration. By choosing wires having different profiles, or by aligning the plurality of wires in different patterns in the expandable member, the degree of bone marrow disruption may be tailored for specific applications or target areas.

The plurality of wires making up the expandable member preferably is made from a nickel-titanium alloy. Such alloys have a super-elastic properties and can be heat set to assume a desired shape above a certain temperature. The methods of carrying out such shape setting of nitinol materials are known to those skilled in the art. Such shape memory wires may be heat treated so that the transformation temperature is between 30° C. and 37° C. (i.e., normal human body temperature). In accordance with one aspect of the present invention, shape memory wires preferably are used in the expandable member of the inventive bone marrow harvesting device as such wires advantageously are bendable 360 degrees, can be heat set and elongated to a nearly straight line without fracture. Alternatively, the plurality of wires also may be made of elastic metal wires.

Figure 11:
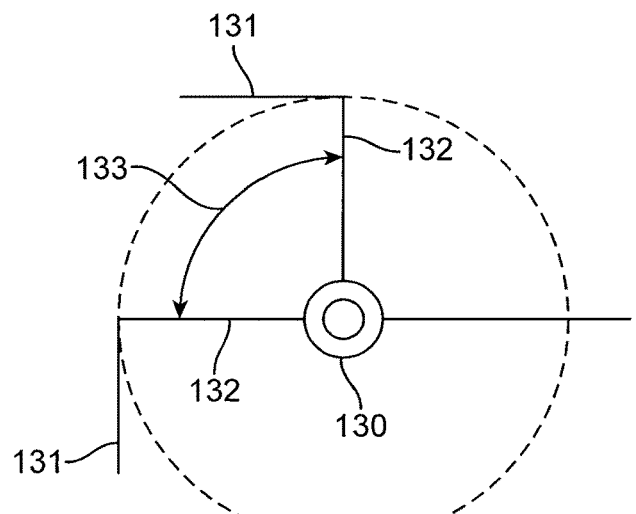
FIG. 11 is an end view of a further alternative embodiment of an expandable member of a bone marrow harvesting device of the present invention.

Referring to FIG. 11, an end view of a distal region of elongated shaft 130 in accordance with one embodiment of the present invention is described. Zig-zag wire 131 is shown at a right angle to strut 132. Zig-zag wire 131 may be oriented clockwise or counterclockwise relative to strut 132. The zig-zag wires may be oriented such that the bends face each other to form a reciprocating pattern. Any number of wires may project from the elongated shaft at an angle 133, as may be allowed by the diameter of elongated shaft 130 with respect to the diameter to the zig-zag wires 131 and struts 132.

Figure 12:
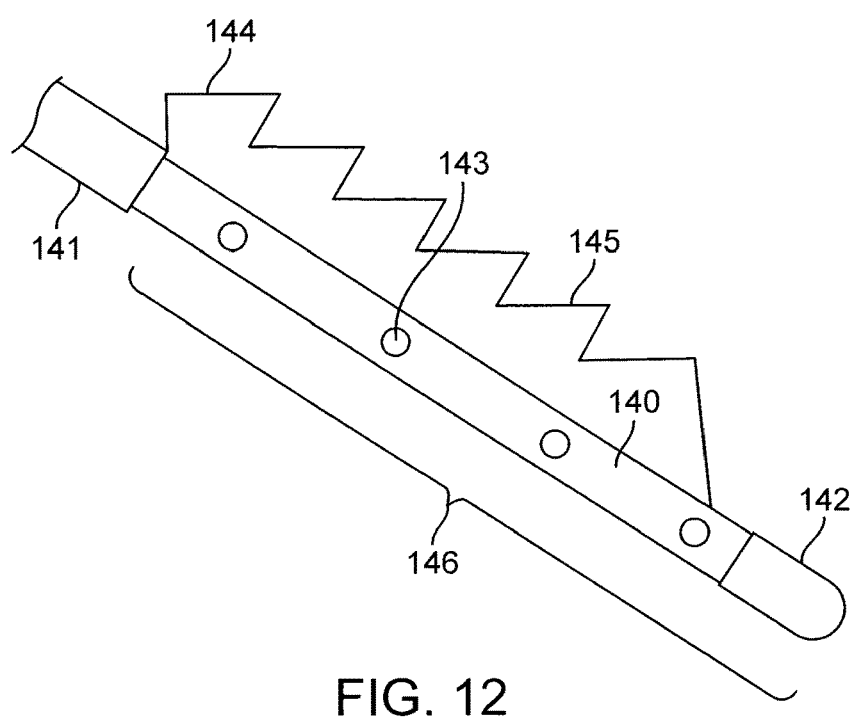
FIG. 12 is a side view of a distal region of a bone marrow harvesting device having one zig-zag wire in accordance with the principles of the present invention.

In FIG. 12, in an alternative embodiment of a bone marrow harvesting device having elongated shaft 140 with outer sheath 141, distal end 142, apertures 143 and single wire 144 bent into zig-zag pattern 145 on distal region 146 is described. Compared to a straight wire configuration, zig-zag patterned wire 144 increases the area of vibration, and allows for varying the area of vibration and the resonance over a larger area. The increase in the area of vibration and resonance is determined by the number and dimension of the zig-zags on each wire, the total number of the plurality of wires, as well as the alignment pattern of the plurality of wires. The number of bends and struts preferably may be determined based on the area and strength of vibration, the amount of bone marrow to be aspirated, and also based on the anatomical structure of the target site.

Figure 13:
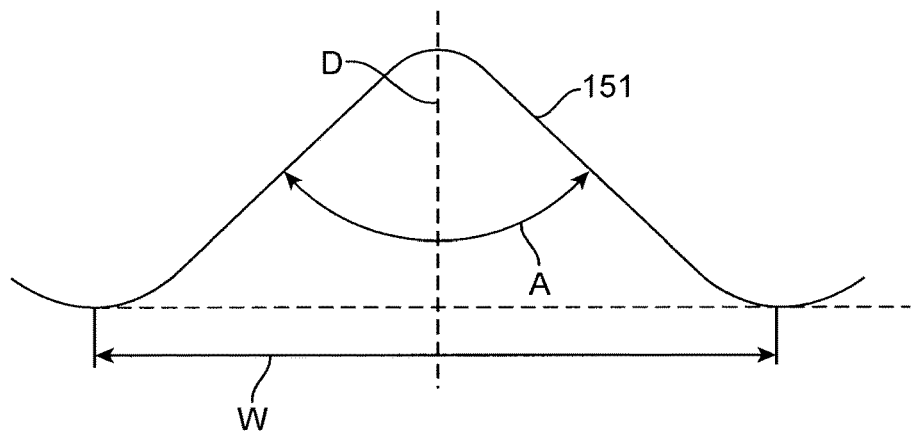
FIGS. 13-15 illustrate designs of various zig-zag wire configurations for use in further alternative embodiments of expandable members suitable for use in the bone marrow harvesting device of the present invention.
Figure 14:
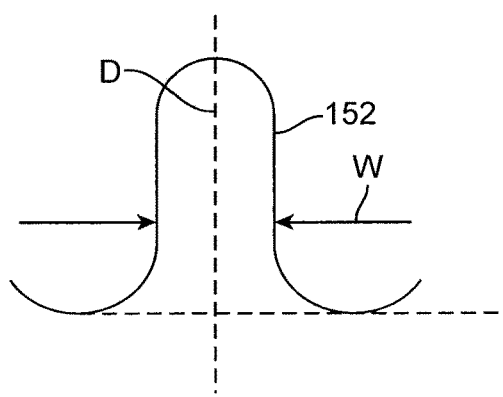
Figure 15:
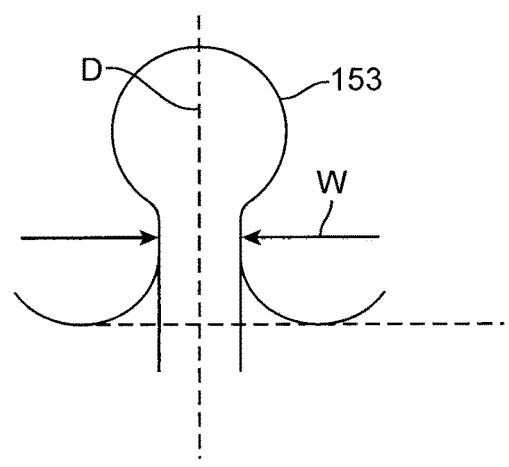

With respect to FIGS. 13-15, different designs of zig-zag wires suitable for use in the expandable member of the present invention are described. In FIG. 13, each zig-zag unit 150 has diameter D, which is a component of the lengths of the struts, and width W. Diameter D and width W define the area of resonance of the vibration generated by the wire. Angle A is formed between the struts and apex, and determines the distance between each apex/zig-zag unit. In FIG. 14, zig-zag unit 152 has a narrow width, and the number of zig-zag units determines the area of resonance of the vibration generated by the wire. In FIG. 15, wire 153 has a spoon shaped zig-zag unit, in which diameter D is larger than width W. This configuration still allows wire 153 to straighten in a collapsed state.

Referring to FIG. 16, vibration assembly 160 suitable for use in the bone marrow harvesting device of the present invention is described. Vibration assembly 160 includes vibration source 161, transmission line 162, illustratively a straight wire, and expandable member 163 as described with respect to the embodiment of FIG. 1. Transmission line 162 is sufficiently rigid to transmit vibration from vibration source 161 to expandable member 163. Expandable member 163 in FIG. 16 is depicted as a plurality of zig-zag wires as shown in the embodiment of FIG. 1 and disposed radially around elongated shaft 101, as depicted in FIG. 2, or alternatively may include any of the expandable members described above.

FIG. 17 depicts an alternative embodiment of vibration assembly, in which vibration source 165 is coupled to expandable member 166 through transmission line 167, in this case helical wire 168. Advantageously, use of helical wire 168 as the transmission line allows the outer sheath and the elongated shaft to bend to fit into different anatomical structures of a patient. FIGS. 18A and 18B depict enlarged views of connecting point C of helical wire 168. Pitch P represents the distance between two adjacent helix turns, measured parallel to the axis of transmission line 167, i.e., the helix between two adjacent apexes of helical wire 168. Pitch P and diameter D define the number of helical turns. For example, a wider pitch (and a smaller diameter) would allow for more helical turns per unit length.

The pitch of the helical wire may be varied. As seen in the alternative embodiment of FIG. 18B, the pitch of the helical wire is wider towards distal end 168', and narrower towards proximal end 168". Such a design creates a more flexible distal tip combined with a stiffer proximal end for increased pushability. As will be understood by one skilled in the art, the length, number and dimension of the helical turns may be adjusted to achieve the desired characteristics of the device, such as the area and strength of the vibration. If a helical wire is used for transmission line 167, it may have a variable pitch along its length to create a variety of configurations tailored to the flexion and/or stiffness of the target site, as well as the anatomical structure of the target site, such as the hip, ribs, femur, etc. Transmission line 167 also may have a tapered shape such that the distal end of the wire is smaller in diameter than the proximal length, or vice versa.

Figure 19A:
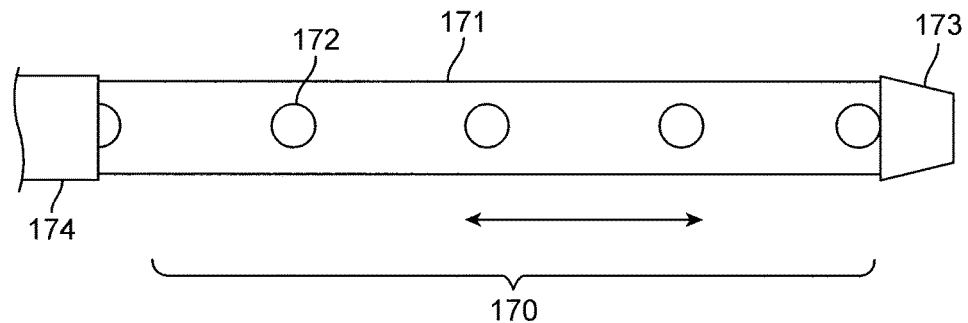
FIGS. 19A-19C are, respectively, a side view of a distal region without an expandable member, with an expandable member in a delivery state, and with the expandable member in a deployed state of another alternative embodiment of a bone marrow harvesting device of the present invention.
Figure 19B:
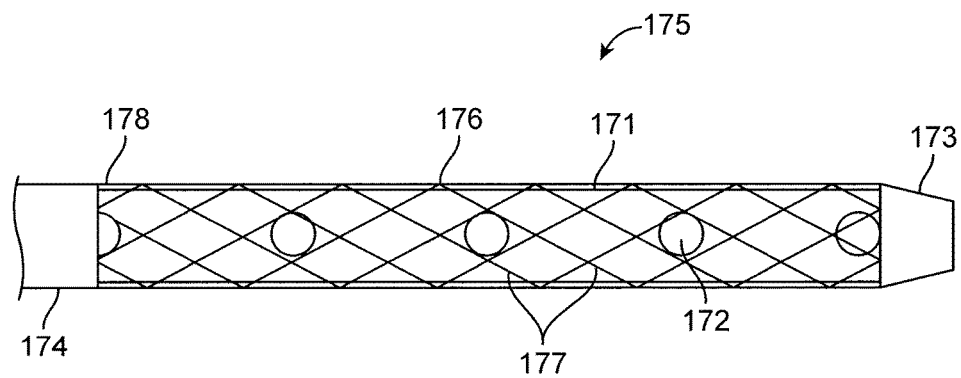
Figure 19C:
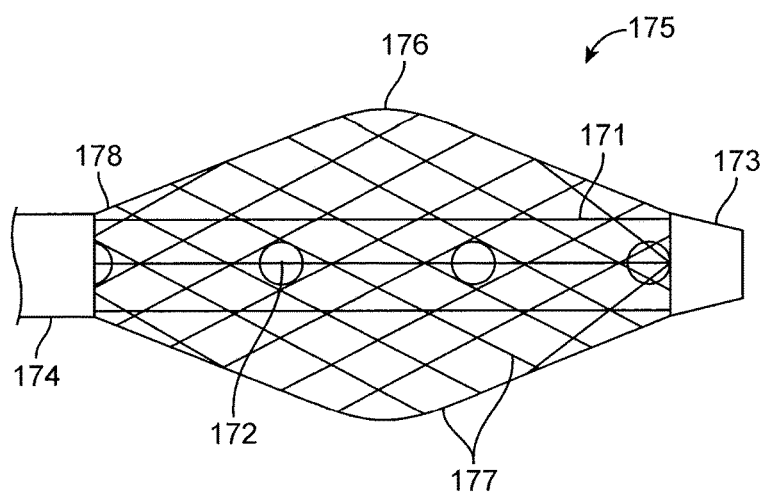

Referring now to FIGS. 19A-19C, a further alternative embodiment of an expandable member suitable for use in the bone marrow harvesting device of the present invention is described. Other aspects of the bone marrow harvesting devices are similar to that of the embodiment described above in connection with FIG. 1, and those details accordingly are omitted in FIGS. 19A-19C for clarity. In FIG. 19A, distal region 170 comprises elongated member 171 having apertures 172 and distal tip 173 disposed for reciprocation in outer sheath 174, as described, for example, with respect to the embodiment of FIG. 1. In FIGS. 19B and 19C, expandable member 175 comprises braided cage 176 composed of a plurality braided wires 177 that overlap one another in an under/over pattern that is repeated circumferentially. The plurality of braided wires 177 are affixed to distal tip 173, while proximal ends 178 of the braided wires 177 extend within outer sheath 174, where they are coupled via a transmission line to a vibration source, as described above with respect to FIGS. 16 and 17. Because braided wires 177 are not secured to one another, the wires move relative to each other within a relatively small range, enabling the wire braid to bow outwards, when proximal ends 178 and distal tip 173 are drawn together by relative movement between elongated member 171 and outer sheath 174, or alternatively, when outer sheath 174 is retracted proximally, as depicted in FIG. 19C.

Similar to the zig-zag wire embodiment, braided cage 176 is configured to be vibrated in its expanded configuration. When the braided cage is vibrated, it induces a 360 degree vibrational field substantial similar to the shape of braided cage 176. To achieve the desired vibration characteristics, the number of wires used, and the pitch and diameter of the wires, may be adjusted. Braided cage 176 may be made of heat set nitinol wires, metal wires, or any other semi-rigid material that permits the transfer of vibration along the length of the wires, for example, nylon, polyimide, and Elgiloy strands. Braided cage 176 may be affixed to elongated shaft 171 or may be manufactured as a separate piece and coupled to the device prior to use.

Still referring to FIGS. 19A-19C, braided cage 176 may be expanded by retracting elongated shaft 171 proximally, thereby shortening the distance between proximal ends 178 of wires 177 and distal tip 173. Alternatively, if the proximal end of braided cage 176 is affixed to the distal end of outer sheath 174, the braided cage may be expanded by holding elongated shaft 171 stationary and advancing outer sheath 174 in a distal direction.

In the expanded configuration shown in FIG. 19C, braided cage 176 preferably has a larger central diameter in the mid-region, with gradually tapered flanks towards the proximal and distal ends. The shape and dimension of the braided cage may be adjusted by increasing or shortening the distance between the proximal and distal ends of the braided cage, thus adjusting the degree of vibration transferred to, and efficacy of removal of, the bone marrow. As the diameter of the mid-region increases, it is expected that vibrations transmitted from the vibration source will be emitted to a larger area but with reduced intensity. In an expanded configuration, braided cage 176 may assume a cross section shape that is round, oval, elliptical, or any irregular shape with tapered proximal and distal ends.

Preferably, braided cage 176 may be formed of nickel-titanium wires that have been heat set to an expanded shape with a larger central diameter in the mid-region, for example, from about 3 cm to about 6 cm, and gradually tapered diameters towards the proximal and distal ends, for example, from about 1 cm to about 2 cm at the most distal ends. When the braided cage is expanded to the heat-set diameter, the elongated shaft is locked in place, and the braided cage can be pushed into any shaped cavity without collapsing. As an example, the braided cage may be elongated from a circular cross sectional shape to an oval cross sectional shape, without completely collapsing. Alternatively, the shape of the braided cage may be controlled by the relative position of the outer sheath and the elongated shaft. When the elongated shaft is retracted proximally, it may be stopped by the distal end of the outer sheath, thereby urging the braided cage into an expanded configuration. Braided cage 176 preferably includes radiopaque markers to assist in placement and/or expansion of the device under fluoroscopic visualization. Also, distal tip 173 may be radiopaque. As a further alternative, braided cage 176 may be constructed of sufficiently thick wires, e.g., between 0.003 to 0.005 inches in diameter, that the cage as a whole is so dense, in combination with the elongated shaft, that it is radiopaque.

Figure 20:
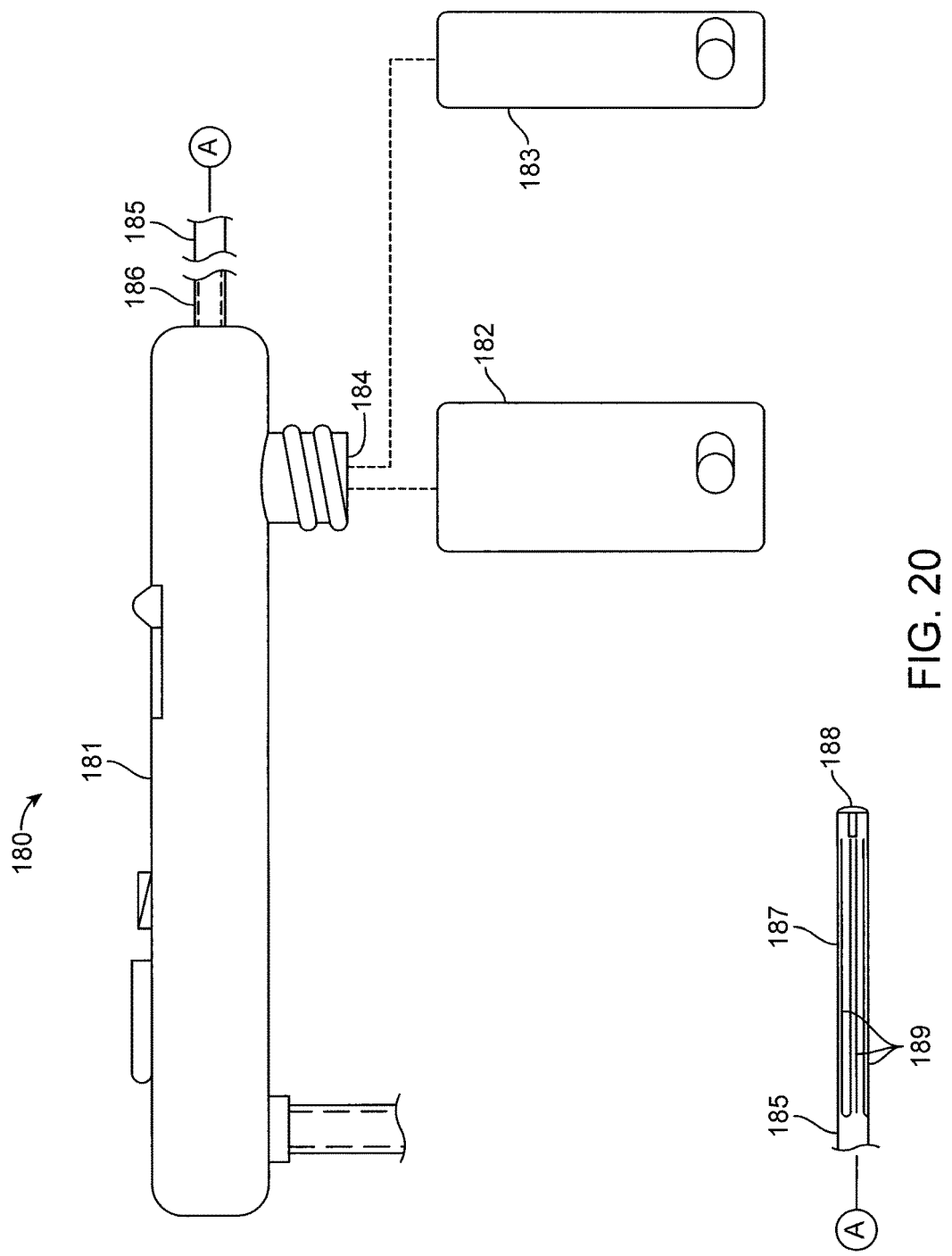
FIG. 20 is a side view of the proximal end and the distal end of a bone marrow harvesting device of the present invention.

Referring now to FIG. 20, another alternative embodiment of a bone marrow harvesting device constructed in accordance with the principles of the present invention is described, which device allows one-handed actuation of the expandable member. Bone marrow harvesting device 180 includes housing 181, motorized module 182 and vibration module 183, which may be removably coupled to housing 181 via connector 184. Elongated shaft 185 is slidably disposed in housing 181, with outer sheath 186 affixed to housing 181 and slidably disposed over elongated shaft 185. Expandable member 187 is affixed on elongated shaft 181 near distal end 188, which may include sharpened cutting edges that serve as a drill bit. Expandable member 187 is made of plurality of wires 189, as described for preceding embodiments, and may transition between a collapsed state and an expanded state. When plurality of wires 189 are stretched, as shown in FIG. 20, expandable member 187 assumes the collapsed state (the expanded states is discussed below in connection with FIG. 21B). The structure and function of expandable member 187 and plurality of wires 189 in this embodiment is substantially the same as those described in connection with preceding embodiments, e.g., FIG. 1. Alternatively, the struts could be integrally formed in the distal region of the outer sheath, e.g., by providing longitudinal slits in outer sheath 186 to form wire-like struts 189, and then heat-setting those struts to deploy to an expanded diameter when elongated shaft 185 is retracted proximally.

In operation, motorized module 182, when employed, is coupled to connector 184 to transmit rotational force to distal end 188 through expandable member 187 to penetrate body tissue, for example, bones or dense tissue around a target site of a patient. Once expandable member 187 is advanced to the vicinity of the target site, motorized module 182 may be disconnected from connector 184 and replaced with vibration module 183. Vibration module 183 is configured to transmit vibrational force to plurality of wires 189 to disrupt dense bone marrow. In a preferred embodiment, expandable member 187 assumes the collapsed state during tissue penetration, and is expanded during bone marrow disruption. Expandable member 187 further may comprise a cut-off switch configured to prevent inadvertent rotation when the expandable member is in the expanded state. After a desired amount of bone marrow has been extracted, expandable member 187 may be collapsed and removed.

As seen in FIGS. 21A and 21B, expandable member 187 may be transitioned between the expanded and collapsed states by operating knob 190, which is disposed in slot 191. When knob 190 is pushed distally, as shown in FIG. 21A, plurality of wires 189 are straightened and lie substantially flush along elongated shaft 185, thereby assuming the collapsed state. When knob 190 is retracted proximally, as shown in FIG. 21B, expandable member 187 assumes the expanded state, in which plurality of wires 189 transition to a preset zig-zag form, as shown in FIG. 21B, and expose apertures 192 in elongated shaft 185.

Knob 190 may be coupled to elongated shaft 185. By pushing knob 190 distally, elongated shaft 185 moves distally, thereby straightening plurality of wires 189. By retracting knob 190 proximally, elongated shaft 185 moves proximally, thereby expanding plurality of wires 189. Knob 190 may be directly attached to elongated shaft 185, or may be coupled to elongated shaft 185 via a wheel, a shaft or other suitable connecting member. The other aspects of expandable member 187 are substantially the same as those described in connection with preceding embodiments.

Figure 22:
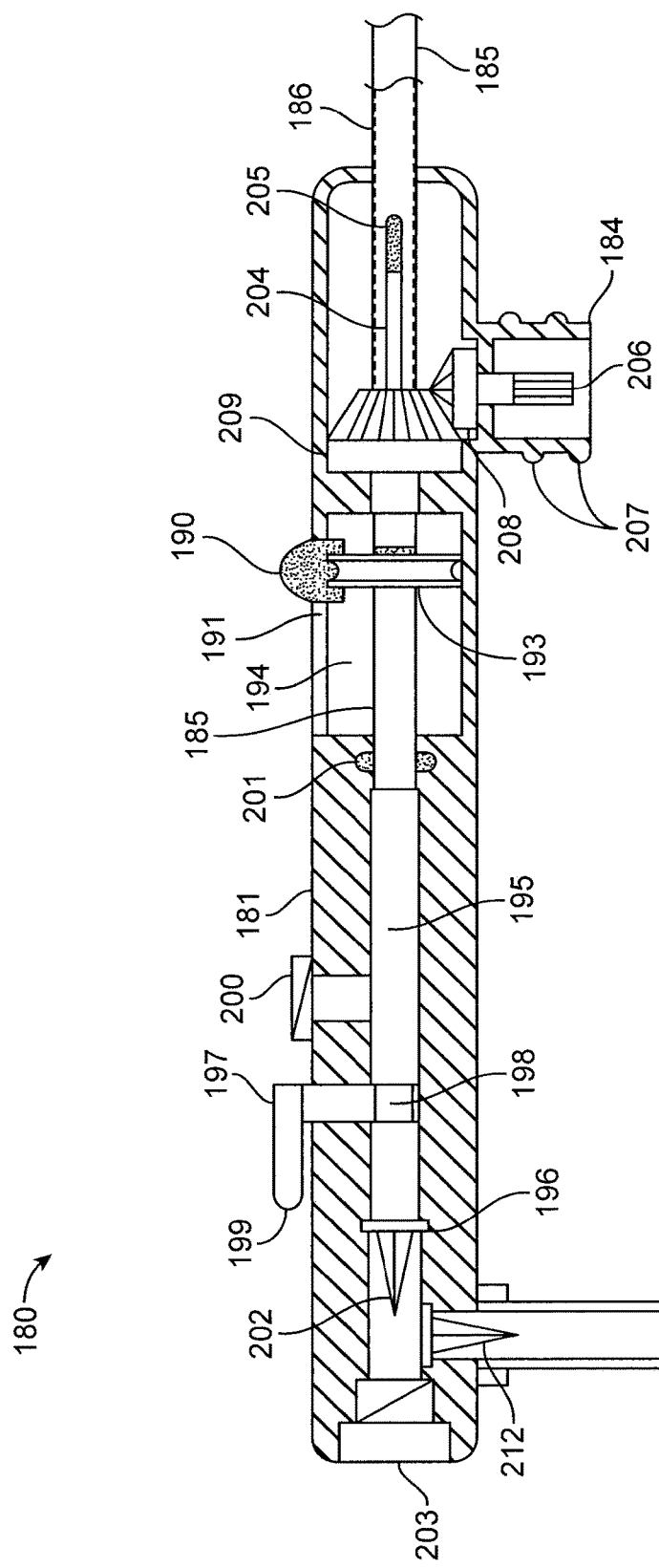
FIG. 22 is a sectional view of the housing of the bone marrow harvesting device of FIG. 20.

FIG. 22 is a side sectional view of bone marrow harvesting device 180 of FIGS. 20-21. Knob 190 engages disk 193, which is coupled to elongated shaft 185, for example, by welding, gluing, or pinning. Disk 193 is disposed in channel 194 of housing 181, with knob 190 extending out of housing 181 through slot 191. Pushing or retracting knob 190 within slot 191 causes disk 193 and elongated shaft 185, to which it is coupled, to move in the corresponding direction. Elongated shaft 185 may be locked in place when knob 190 reaches the distal-most end of slot 191. Disk 193 includes features that maintain engagement with knob 190 while still permitting elongated shaft 185 to rotate during the bone drilling procedure, as described in detail below.

Elongated shaft 185 is slidably disposed within working lumen 195 of housing 181. Working lumen 195 is formed in housing 181 and is in fluid communication with valve 196 at its proximal end, and merges with channel 194 at its distal end. Stopcock 197 includes plug 198 that seals working lumen 195 when being actuated, and handle member 199 mounted on housing 181. When stopcock 197 is in its open position, i.e., when the plug 198 is out of the path of working lumen 195, it allows fluid communication between valve 196 and the portion of working lumen 195 distal to stopcock 197, thereby allowing bone marrow to be aspirated, as further described below. When stopcock 197 is in its closed position, i.e., when plug 198 blocks working lumen 195, fluid communication between valve 196 and the portion of working lumen distal to stopcock 197 is prevented. A fluid syringe (not shown) then may be attached to fluid valve 200 to inject a fluid into working lumen 195 and elongated shaft 185, which fluid may exit from the plurality of through-wall apertures (not shown) of elongated shaft 185 and into the target site. Fluid valve 196 may be a self-sealing valve.

Housing 185 further comprises O-ring 201 disposed between the proximal end of elongated shaft 185 and the inner surface of working lumen 195. O-ring 201 seals against fluid in channel 194 from entering into working lumen 195, or vice versa.

Valve 196 is sealingly connected to the distal end of syringe channel 202 to allow aspiration of bone marrow from working lumen 195 to syringe channel 202. Aspiration syringe receptacle 203, which may be a Luer Lock, is disposed at the proximal end of syringe channel 203 to receive a syringe (not shown). Valve 196 may comprise a duckbill valve or any other suitable one-way valve known in the art.

The elongated shaft and the outer sheath preferably are locked together during drilling. Outer sheath 186 preferably includes a solid distal end having groove 204 that engages key 205 of elongated shaft 185, such that elongated shaft 185 and outer sheath 186 are securely attached together and rotate together when motorized module (see 182 of FIG. 20) is in operation.

As described with respect to FIG. 20, motorized module 182 or vibration module 183 is configured to engage connector 184. Connector 184 preferably has a substantially cylindrical body extending perpendicularly to the longitudinal axis of housing 181, and drive shaft 206 disposed inside of the cylindrical body. The module may comprise threads for engaging connector 184 via plurality of threads 207 disposed on the outer surface of connector 184. Drive shaft 206 may comprise an octagonal drive shaft, and is coupled to pinion gear 208, which in turn drives gear shaft 209 affixed to outer sheath 186. The foregoing gear arrangement is exemplary, and other arrangements will be apparent to those of skill in mechanical design for transferring rotational or vibratory force from the motorized module 182 or vibration module 183 to expandable member 187.

As will be apparent from the foregoing description of the embodiment of FIGS. 20-22, bone marrow harvesting device 180 may be used in a drilling mode when coupled to motorized module 182 and an aspiration mode when coupled to vibration module 183. When device 180 is employed in a drilling mode, motorized module 182 is attached to housing 181, and knob 190 is pushed distally in slot 191, thereby causing expandable member 187 to assume the collapsed state, with plurality of wires 189 straightened over the distal portion of elongated shaft. Motorized module 182 then is activated to transmit rotational force to distal tip 188 through drive shaft 206, gears 208 and 209, outer sheath 186 and elongated shaft 185, thereby causing the cutting edges of distal tip 188 to penetrate tissue and bone of the patient's body.

Once distal tip 188 of device 180 has penetrated to a desired location in the patient's body, for example, as determined by visualizing radiopaque features of distal tip 188 or elongated shaft 185 or expandable member 187 under fluoroscopic guidance, or by using fiducial markers on elongated shaft 181, motorized module 182 is deactivated and removed, and vibration module 183 is coupled to housing 181. Knob 190 is retracted proximally in slot 191, thereby causing expandable member 187 to transition to the expanded state, with plurality of wires 189 assuming their preset zig-zag shape. Vibration module 183 then is activated to vibrate plurality of wires 189 and disrupt bone marrow at the target site.

Figure 23A:
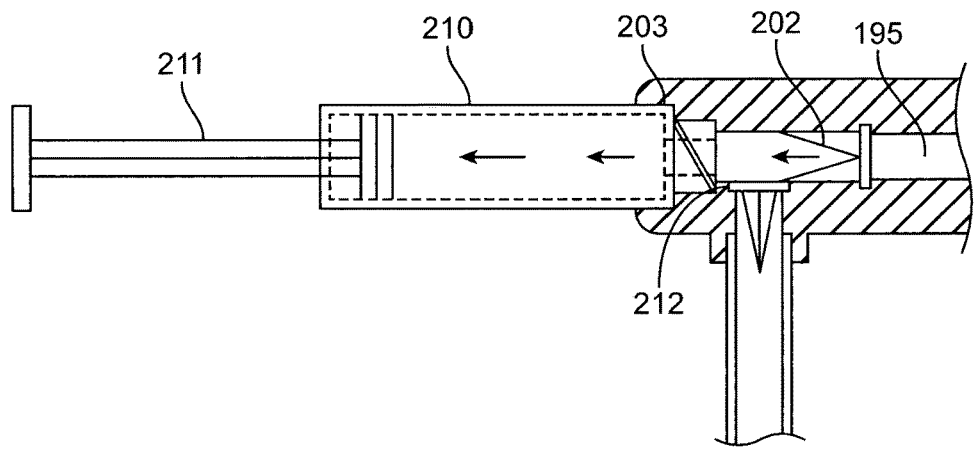
FIGS. 23A-23B are, respectively, side sectional views illustrating use of a syringe to aspirate bone marrow from a target site using the device of FIG. 20.
Figure 23B:
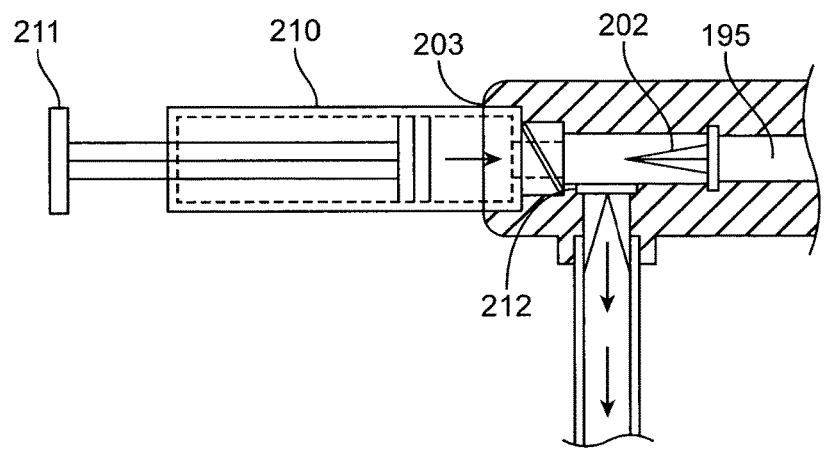

Referring now also to FIGS. 23A and 23B, aspiration syringe 210 may be fluidly connected to aspiration syringe receptacle 203 of housing 180 to aspirate disrupted bone marrow. To aspirate bone marrow, stopcock 197 (see FIG. 22) is opened to allow flow of bone marrow from working lumen to aspiration syringe 210. An irrigation syringe (not shown) may be attached to housing 181 via syringe receptacle 200 (see FIG. 22) for injecting a fluid into the elongated shaft and/or the target site to facilitate vibration, aspiration or carry out therapeutic treatment. The irrigation syringe also may be used to aspirate fluid and/or bone marrow. As shown in FIG. 23A, once aspiration syringe 210 attached to aspiration syringe receptacle 203, plunger 211 is retracted proximally, causing valve 202 to open and bone marrow to move from within elongated shaft 181 through working lumen 195 into aspiration syringe 210. As depicted in FIG. 23B, when plunger 211 is pushed distally, valve 202 closes, and the extracted bone marrow in aspiration syringe 210 is moved into a reservoir (similar to reservoir 110 of FIG. 1) through reservoir valve 212. Reservoir valve 212 may be a duckbill valve or any other suitable one-way valve known in the art. The reservoir may be an I.V. bag or any other sterile collection vessel.

Figure 24:
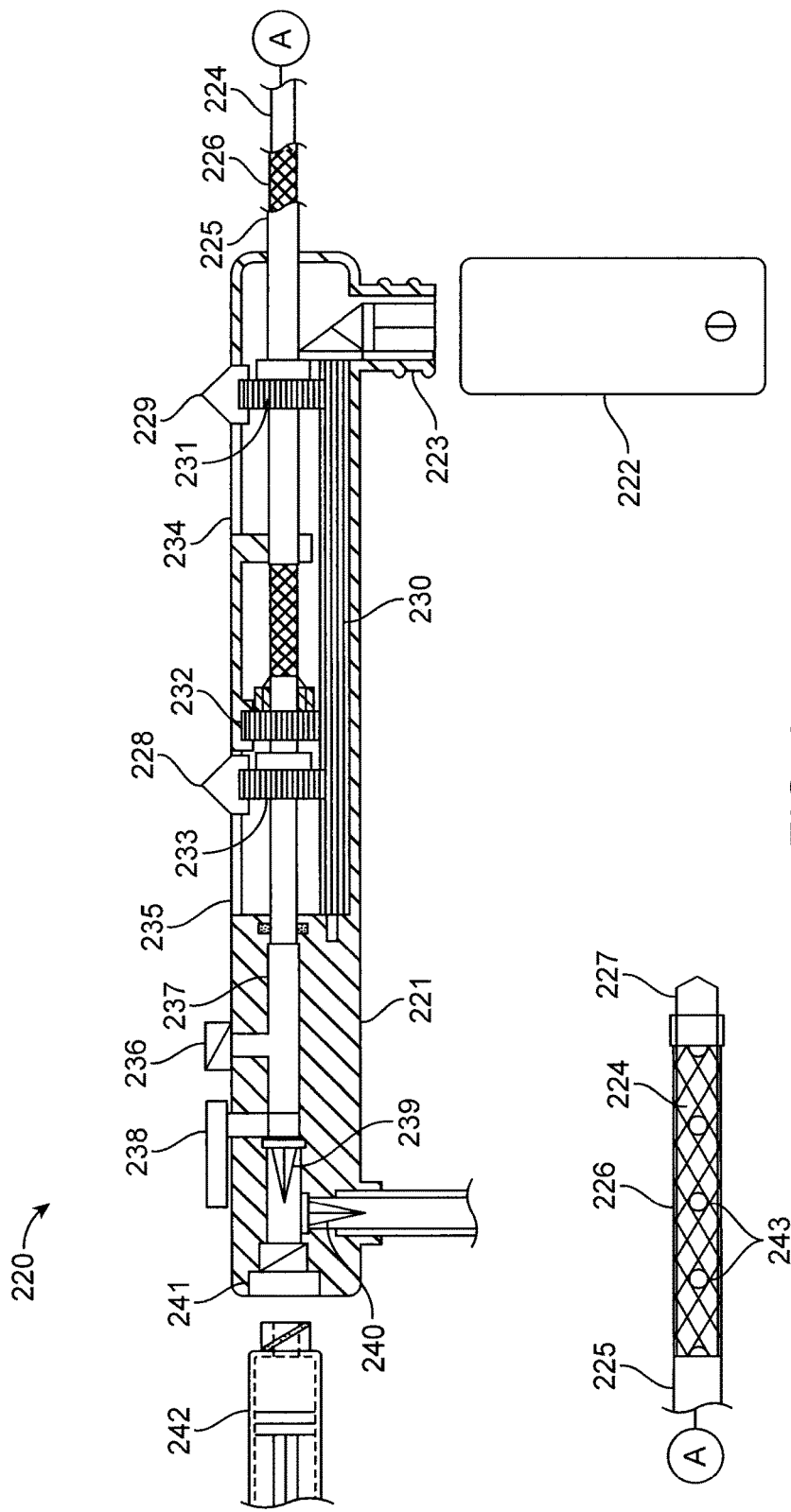
FIG. 24 is a side sectional view of an alternative embodiment of a bone marrow aspiration of the present invention.
Figure 25A:
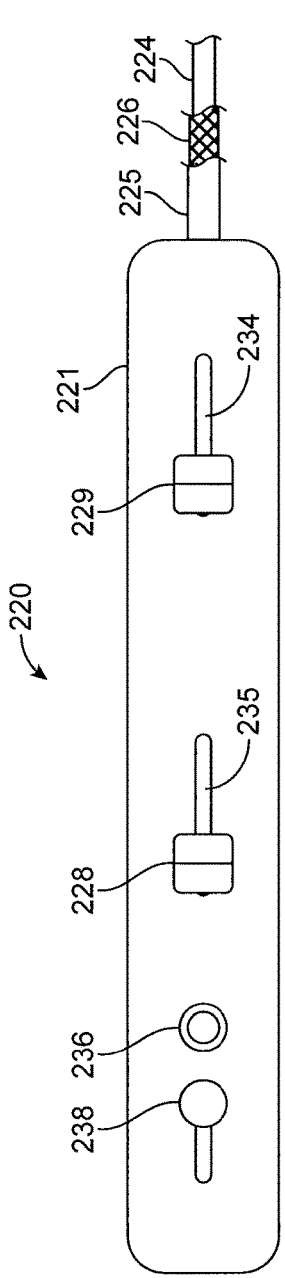
FIGS. 25A and 25B are, respectively, top and side sectional views and handle portion of the bone marrow harvesting device of FIG. 24 in an aspirating mode, and of the expandable member in an expanded configuration.
Figure 25B:
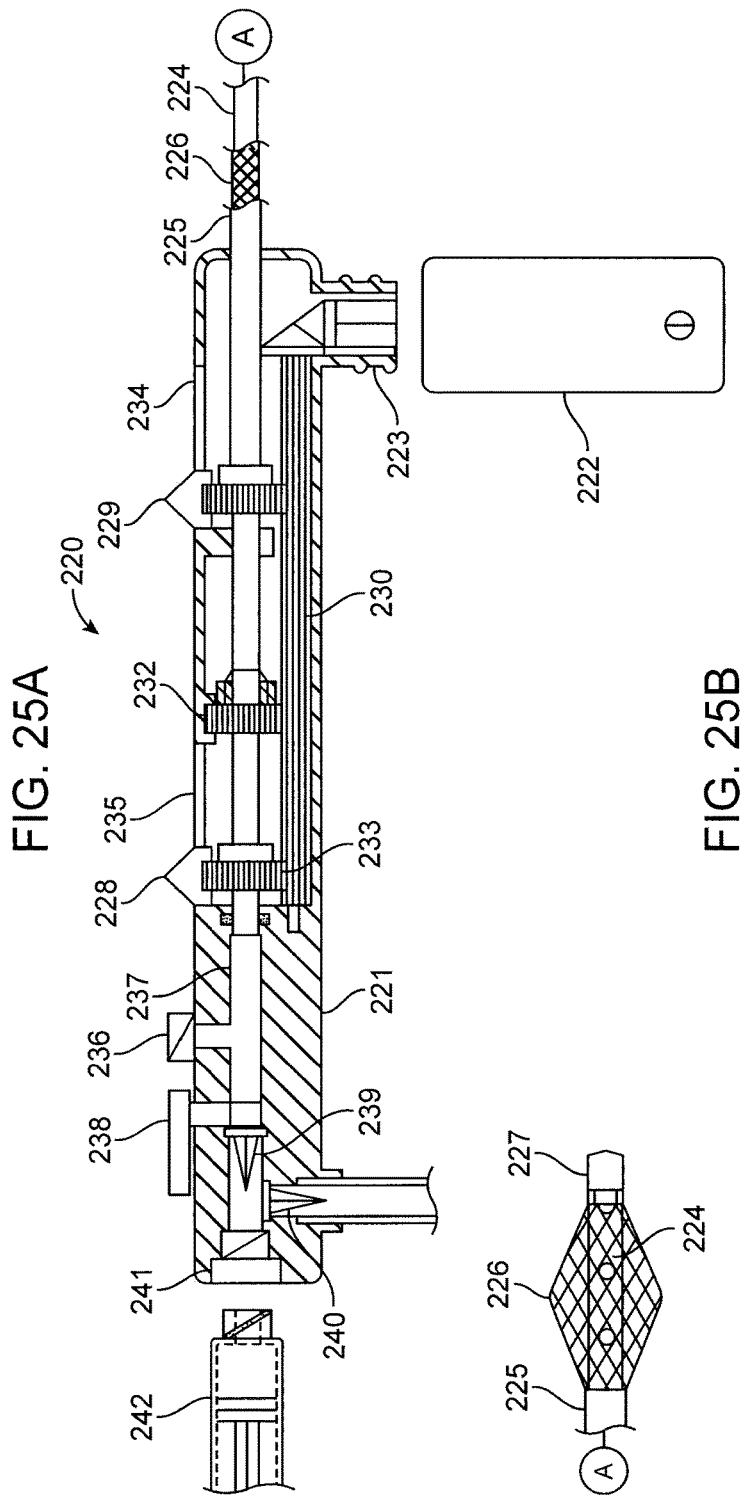

Referring now to FIGS. 24, 25A and 25B, another embodiment of a bone marrow harvesting device constructed in accordance with the principles of the present invention is described. As seen in FIG. 24, bone marrow harvesting device 220 comprises housing 221, motorized or vibrational module 222 configured to be removably coupled to housing 221 via connector 223, elongated shaft 224 slidably received within outer sheath 225, which is in turn slidably received within housing 221, and expandable braided cage 226 disposed over the distal region of elongated shaft 224. Drilling tip 227 is disposed at the distal end of elongated shaft 224. The structure and function of expandable braided cage 226 are substantially the same as the embodiments described in FIGS. 19A-C. Similar to the expandable member described in FIG. 20, elongated shaft 224 and outer sheath 226 preferably are securely attached to each other via a key/slot arrangement such that they rotate together.

FIG. 24 shows expandable braided cage 226 in the collapsed state while FIG. 25B shows the cage in the expanded state. Expansion and collapse of expanded braided cage 226 is controlled by knobs 228 and 229 on housing 221. Housing 221 includes within it main drive gear 230, which is drivingly connected to three smaller gears 231, 232 and 233. Gear 231 is affixed to outer sheath 225 and knob 229, such that the position of knob 229 within slot 234 controls positioning of the distal end of outer sheath 225. Gear 233 is affixed to knob 228 and elongated shaft 224, and its position within slot 235 controls positioning of elongated shaft 224 and distal tip 227. Gear 232 is affixed to the proximal end of expandable braided cage 226. When knob 228 is pushed distally, gear 233 and elongated shaft 224 attached thereto also move distally, thereby stretching expandable braided cage 226 to assume the collapsed state. When expandable braided cage 226 is in the collapsed state, knob 229 may be pushed distally, thereby moving outer sheath 225 over the collapsed expandable braided cage 226. For expandable braided cage 226 to transition to its expanded state, knob 229 is retracted proximally along slot 234 to uncover expandable braided cage 226, and then knob 228 is retracted proximally in slot 235 to retract elongated shaft 224 and expand expandable braided cage 226.

The proximal portion of housing 221 (distal to knob 228 and gear 233) and connector 223 are substantially similar to the components of the embodiment of FIG. 20, and include irrigation port 236 that is in fluid communication with working lumen 237, stopcock 238, one-way valves 239 and 240 and aspiration syringe receptacle 241. Aspiration syringe receptacle 241 may be coupled to aspiration syringe 242, such that the foregoing components may be used as described above with respect to the corresponding components to aspirate bone marrow through apertures 243 in the distal region of elongated shaft 224, as described with respect to FIGS. 22, 23A and 23B.

As for the embodiment of FIG. 20, expandable braided cage 226 preferably is used in the collapsed state (see FIG. 24) for penetrating tissue. In particular, motorized module 222 may be attached to housing 221 and actuated to provide rotation to elongated shaft 224 and distal tip 227 to function as a drill tip in penetrating tissue and a targeted source of bone marrow. Once distal tip 227 is positioned at a desired location, as may be determined under fluoroscopic visualization, motorized module 222 may be disconnected from connector 223 and replaced with a vibration module similar to vibration module 183 of FIG. 20. Expandable braided cage 226 then is deployed by moving knobs 228 and 229 as described above, and the vibration module may be actuated to transmit vibration through gears 230, 232 and expandable braided cage 226 to disrupt the bone marrow. An irrigation syringe may be coupled to irrigation port 236 to inject a suitable biocompatible fluid through through-wall apertures in the distal region of the elongated shaft 224, and aspiration syringe 242 may be used to aspirate bone marrow through expandable braided cage 226, elongated shaft 224 and to a reservoir (not shown).

Distal tip 227 may include cutting edges or flutes that serve as a drill tip to permit the distal region of the device to penetrate tissue and bone to reach a targeted bone marrow source. Preferably, distal tip 227 is affixed to the distal end of elongated shaft 224, where it supports the distal end of expandable braided cage 226. Preferably, distal tip 227, elongated shaft 224 and expandable braided cage 226 are assembled together, for example, by gluing, crimping and/or welding. Elongated shaft 224, expandable braided cage 226, and/or distal tip 227 further may include wings, protrusions, keys, grooves, or any other arrangement for nesting elongated shaft 224 within outer sheath 225, which outer sheath 225 includes a corresponding arrangement for engaging the wings or protrusions, or nesting in the slots or grooves.

Referring now to FIGS. 26A and 26B, further structural details of a distal tip arrangement suitable for use in the bone marrow harvesting device of the present invention are described. Distal tip 250 includes sharpened cutting edge 251 and at least one, and preferably four, keys 252. Outer sheath 253 includes corresponding slot(s) 254 for securely receiving key(s) 252 when distal tip 250 and outer sheath 253 are brought together. Distal tip 250 is connected to elongated shaft 255 and expandable braided cage 256. When outer sheath 253 and distal tip 250 are engaged via the key/slot arrangement, the two components rotate in unison and effectively transmit torque to cutting edge 251. When the outer sheath 253 is retracted it disengages slot(s) 254 from key(s) 252 of the distal tip uncovering expandable braided cage 256, which is then expanded to disrupt and/or aspirate bone marrow.

Figure 27:
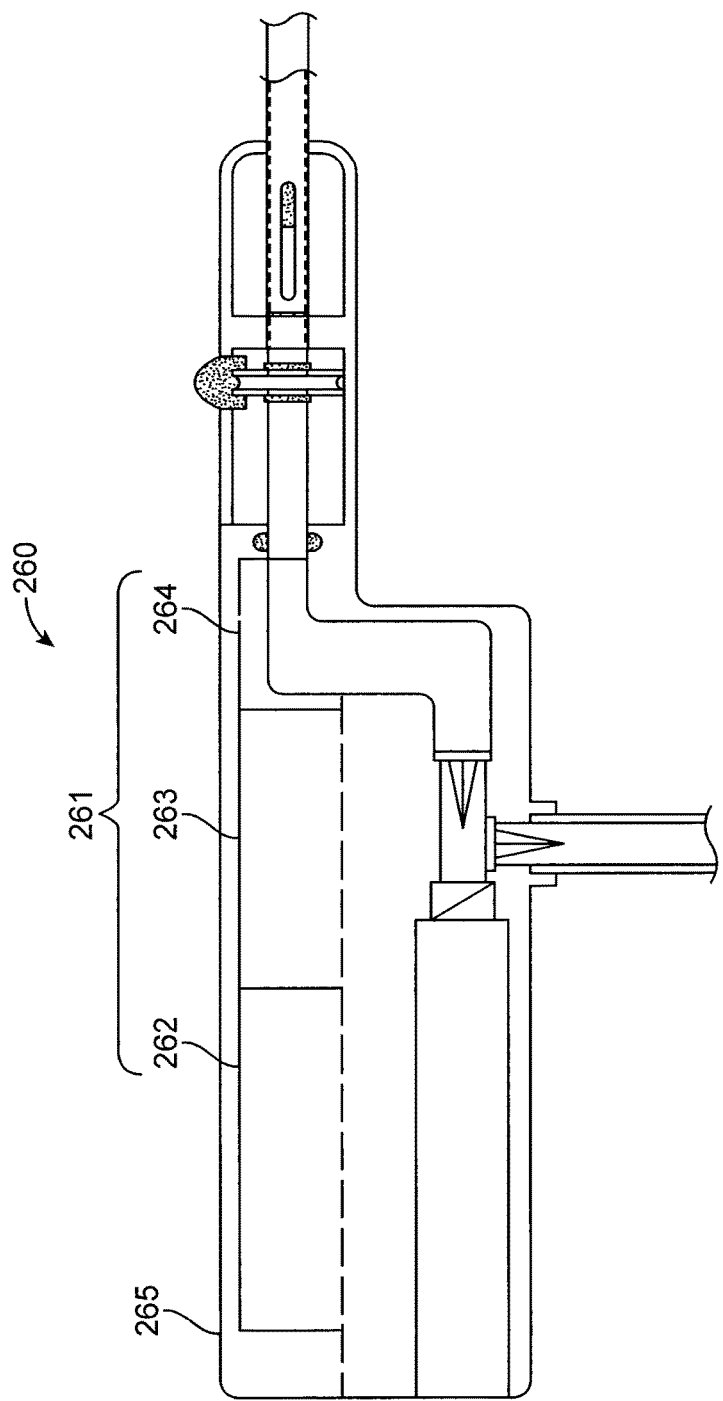
FIG. 27 is side sectional view of a further embodiment of a bone marrow harvesting device of the present invention.

With respect to FIG. 27, a further alternative embodiment of a bone marrow harvesting device of the present invention is described in which the vibration module and/or the motorized module are located within device 260. Module 261 is located in a proximal portion of housing 262, and transmits energy to the expandable member to disrupt bone marrow or to penetrate tissue. The expandable member may be any of the preceding embodiments set forth in this specification. Module 261 may comprise battery 262, transducer 263, and transmission member 264. Transducer 263 may comprise, e.g., an ultrasonic transducer, a piezoelectric transducer, or a vibration motor. Transmission member 264 may be arranged to control the output of transducer 263. Other components of bone marrow harvesting device 260 may be as described above with respect to the embodiments of, for example, FIG. 20 or 24.

With respect to FIGS. 28A-28B, an embodiment of transmission member suitable for use in the embodiment of the bone marrow harvesting device of FIG. 27 is described. Transmission member 270 includes helical spring 271 and lever 272, coupled to an elongated shaft 273 and distal tip (not shown) as described hereinabove. Transmission member 270 is coupled at its proximal end to ultrasonic transducer 274. Helical spring 271 in its undeformed state has turns that directly abut one another, such that every coil turn is in direct contact with adjacent neighboring turns, as depicted in FIG. 28A. When helical spring 271 is in its undeformed state, ultrasonic energy may be transmitted through helical spring 271 to the distal tip. During bone marrow aspiration, lever 272 may be advanced distally, thereby expanding helical spring 271 and creating gaps 275 between adjacent turns. In this deformed state, the intensity of the ultrasonic energy to the distal tip is reduced, while gaps 275 permit bone marrow to be aspirated through the expanded spring.

The harvested bone marrow may include a mixed population of various types of undifferentiated cells, including hematopoietic stem cells (HSCs), endothelial progenitor cells (EPCs), and mesenchymal stem cells (MSCs). HSCs are stem cells that form blood and immune cells, and can be readily isolated from bone marrow. MSCs are another type of adult bone marrow derived stem cells with the ability to form cartilage, bone, adipose tissue, and marrow stroma, and are capable of sustained expression of growth factors. Endothelial progenitor cells are primitive bone marrow cells that also are reported to possess the ability to mature into cells that form vessel walls. Additionally, the stem cells may be combined with growth factors such as EGF, FGF, GDF, IGF, PDGF, and VEGF to promote cell differentiation.

Those skilled in the art will appreciate that the invention can be practiced in other than the described embodiments, which are presented for purposes of illustration and not of limitation.

What is claimed is:

1. A bone marrow harvesting device, comprising:
an elongated shaft comprising a distal region, a proximal region, and a lumen extending therebetween, the distal region of the elongated shaft comprising at least one through-wall aperture in fluid communication with the lumen, the distal region of the elongated shaft sized and shaped to be delivered to a biological source of bone marrow;
an expandable member disposed along the distal region of the elongated shaft, the expandable member configured to transition between a collapsed stated for delivery to the biological source of bone marrow and an expanded state for disrupting the bone marrow; and
a vibration source coupled to the expandable member, the vibration source configured to vibrate the expandable member to disrupt the bone marrow,
wherein the at least one through-wall aperture is positioned within the expandable member, when the expandable member is transitioned to the expanded state, so that bone marrow disrupted by the expandable member is aspirated through the at least one through-wall aperture and lumen for collection via the proximal region.

2. The bone marrow harvesting device of claim 1, further comprising an outer sheath configured to reciprocate relative to the elongated shaft.

3. The bone marrow harvesting device of claim 1, wherein the expandable member comprises a plurality of wires, each wire having a zig-zag pattern.

4. The bone marrow harvesting device of claim 3, wherein the plurality of wires comprise a shape memory alloy.

5. The bone marrow harvesting device of claim 1, wherein the expandable member comprises a braided cage.

6. The bone marrow harvesting device of claim 1, further comprising an aspiration member and a reservoir coupled to the proximal region and in fluid communication with the lumen.

7. The bone marrow harvesting device of claim 6, further comprising a valve disposed between the aspiration member and the lumen.

8. The bone marrow harvesting device of claim 1, wherein the vibration source comprises at least one of an ultrasonic transducer, a piezoelectric transducer, a motor, and a linear resonant actuator.

9. The bone marrow harvesting device of claim 1, further comprising at least one fiducial mark disposed in the proximal region.

10. The bone marrow harvesting device of claim 1, wherein the distal region of the elongated shaft is deflectable.

11. The bone marrow harvesting device of claim 1, wherein at least a portion of the distal region of the elongated shaft is radiopaque.

12. A method for harvesting bone marrow from a patient, the method comprising:

advancing a bone marrow harvesting device to a biological source of bone marrow in the patient, the bone marrow harvesting device comprising an elongated shaft having a distal region, a proximal region, and a lumen extending therebetween, the distal region comprising at least one through-wall aperture in fluid communication with the lumen;

expanding an expandable member disposed over the distal region;

disrupting the bone marrow by vibrating the expandable member using a vibration source coupled to the expandable member;

aspirating the bone marrow through at least one through-wall aperture via the lumen.

13. The method of claim 12, wherein expanding the expandable member comprises expanding a plurality of wires, each wire having a zig-zag pattern.

14. The method of claim 12, wherein expanding the expandable member comprises expanding a braided cage.

15. The method of claim 12, further comprising moving the bone marrow from the lumen to a reservoir in fluid communication with the lumen.

16. The method of claim 12, further comprising introducing a liquid through the lumen to the biological source of bone marrow.

17. The method of claim 16, wherein introducing a liquid comprises introducing at least one of saline, heparinized saline, lactated ringer solution, growth factors, anti-inflammatory agents, antibiotics, analgesic agents, nucleic acids, cells or any combination thereof.

18. The method of claim 12, wherein at least a portion of the distal region of the elongated shaft is radiopaque and the method further comprises visualizing the location of the distal region under fluoroscopic guidance.

19. The method of claim 12, wherein vibrating the expandable member comprises coupling the expandable member to a vibration source comprising at least one of an ultrasonic transducer, a piezoelectric transducer, a motor or a linear resonant actuator.

20. The method of claim 12 wherein, advancing a bone marrow harvesting device to a biological source of bone marrow comprises rotating the elongated shaft so that a distal tip on the elongated shaft penetrates bone to access the biological source of bone marrow.

* * * * *